US011878001B2

(12) United States Patent
Dolmetsch et al.

(10) Patent No.: US 11,878,001 B2
(45) Date of Patent: Jan. 23, 2024

(54) USE OF MAVOGLURANT IN THE REDUCTION OF COCAINE USE OR IN PREVENTING RELAPSE INTO COCAINE USE

(71) Applicant: NOVARTIS AG, Basel (CH)

(72) Inventors: Ricardo Carl Elciario Dolmetsch, Concord, MA (US); Fabrizio Gasparini, Weiherhofstrasse (CH); Baltazar Gomez-Mancilla, Basel (CH); Donald Johns, Woburn, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/634,991

(22) PCT Filed: Jul. 30, 2018

(86) PCT No.: PCT/IB2018/055664
§ 371 (c)(1),
(2) Date: Jan. 29, 2020

(87) PCT Pub. No.: WO2019/025931
PCT Pub. Date: Feb. 7, 2019

(65) Prior Publication Data
US 2021/0093609 A1    Apr. 1, 2021

Related U.S. Application Data

(60) Provisional application No. 62/539,003, filed on Jul. 31, 2017.

(51) Int. Cl.
*A61K 31/404* (2006.01)
*A61K 45/06* (2006.01)
*A61P 25/36* (2006.01)

(52) U.S. Cl.
CPC ............ *A61K 31/404* (2013.01); *A61K 45/06* (2013.01); *A61P 25/36* (2018.01)

(58) Field of Classification Search
CPC .. A61K 31/404; A61K 45/06; A61K 2300/00; A61P 25/36; A61P 25/30
See application file for complete search history.

(56) References Cited

U.S. PATENT DOCUMENTS

| 4,129,658 | A | 12/1978 | Berthold |
| 5,661,184 | A | 8/1997 | Helton et al. |
| 5,675,008 | A | 10/1997 | Bertsch et al. |
| 6,635,647 | B2 | 10/2003 | Troxler |
| 6,656,957 | B1 | 12/2003 | Allgeier et al. |
| 6,730,689 | B2 | 5/2004 | Quan |
| 6,759,428 | B2 | 7/2004 | Bamberg et al. |
| 6,927,232 | B2 | 8/2005 | Mutel et al. |
| 7,138,404 | B2 | 11/2006 | Mutel et al. |
| 7,157,582 | B2 | 1/2007 | Filla et al. |
| 7,348,353 | B2 | 3/2008 | Gasparini et al. |
| 7,531,541 | B2 | 5/2009 | Conn et al. |
| 8,084,487 | B2 | 12/2011 | Kuesters et al. |
| 8,163,785 | B2 | 4/2012 | Devereux et al. |
| 8,354,447 | B2 | 1/2013 | Markou et al. |
| 8,574,626 | B2 | 11/2013 | Vergez et al. |
| 8,691,849 | B2 | 4/2014 | Cid-Nunez et al. |
| 8,703,809 | B2 | 4/2014 | Gomez-Mancilla et al. |
| 8,835,444 | B2 | 9/2014 | Beattie et al. |
| 9,173,864 | B2 | 11/2015 | Friedman et al. |
| 9,650,377 | B2 | 5/2017 | Behnke et al. |
| 9,770,423 | B2 | 9/2017 | Erickson et al. |
| 10,336,687 | B2 | 7/2019 | Cacciaglia et al. |
| 2001/0056084 | A1 | 12/2001 | Allgeier et al. |
| 2003/0195139 | A1* | 10/2003 | Corsi ............... A61K 45/06 514/1 |
| 2006/0216347 | A1 | 9/2006 | Stroppolo et al. |
| 2008/0207749 | A1 | 8/2008 | Rouzade-Dominguez et al. |
| 2009/0215744 | A1 | 8/2009 | Brown et al. |
| 2010/0160320 | A1 | 6/2010 | Fan et al. |
| 2011/0201629 | A1 | 8/2011 | Atkinson et al. |
| 2012/0039999 | A1 | 2/2012 | Chatterji et al. |
| 2012/0040008 | A1 | 2/2012 | Chatterji et al. |
| 2012/0046232 | A1 | 2/2012 | Kalivas et al. |
| 2014/0088105 | A1 | 3/2014 | Beattie et al. |
| 2015/0141462 | A1 | 5/2015 | Olive |
| 2016/0000736 | A1 | 1/2016 | Cohen et al. |
| 2016/0128979 | A1 | 5/2016 | Thoma et al. |

(Continued)

FOREIGN PATENT DOCUMENTS

| CA | 2484248 A1 | 3/1994 |
| CN | 102119151 A | 7/2011 |

(Continued)

OTHER PUBLICATIONS

Kiluk et. al., Addiction, vol. 105, pp. 2120-2127, publ. 2010, Society for the Study of Addiction (Year: 2010).*
McKetin et. al., Drug & Alcohol Rev., vol. 33, pp. 436-445, publ. Jul. 2014, Australasian Professional Society on Alcohol and other Drugs (Year: 2014).*
Haile et. al., Behav. Genet., vol. 37, pp. 119-145, publ. 2007, Springer (Year: 2007).*
Adams et. al., Case Reports in Psych., article ID 731638, pp. 1-8, publ. 2012 (Year: 2012).*
Novartis, Study to Investigate Whether AFQ056 Reduces Cocaine Use in Patients Diagnosed With Cocaine Use Disorder (CUD), ClinicalTrials.gov, https://clinicaltrials.gov/ct2/show/results/NCT03242928?term=CAFQ056x2201&draw=2&rank=1, update published Oct. 8, 2021, pp. 1-16 (Year: 2021).*

(Continued)

*Primary Examiner* — Sarah Pihonak
(74) *Attorney, Agent, or Firm* — Millen, White, Zelano & Branigan, P.C.; Ryan R. Pool

(57) ABSTRACT

The invention relates to the use of mavoglurant, or a pharmaceutically acceptable salt thereof: in the reduction of cocaine use by a cocaine use disorder patient; in preventing relapse into cocaine use by a cocaine use disorder patient; in the promotion of cocaine abstinence by a cocaine use disorder patient; in in the treatment of the symptoms of depression or anxiety associated with cocaine use disorder.

13 Claims, 5 Drawing Sheets

(56) References Cited

U.S. PATENT DOCUMENTS

| | | |
|---|---|---|
| 2021/0069150 A1 | 3/2021 | Galli et al. |
| 2021/0093609 A1 | 4/2021 | Dolmetsch et al. |
| 2021/0187033 A1 | 6/2021 | Boitano et al. |
| 2022/0175793 A1 | 6/2022 | Dolmetsch et al. |

FOREIGN PATENT DOCUMENTS

| | | |
|---|---|---|
| CN | 104520298 A | 4/2015 |
| DE | 2802833 A1 | 7/1979 |
| EP | 1267869 B1 | 5/2004 |
| EP | 1453512 A1 | 9/2004 |
| HU | 0400570 A | 6/2004 |
| JP | 5340766 A | 4/1978 |
| JP | 2003-525902 | 9/2003 |
| JP | 2003525902 A | 9/2003 |
| JP | 2005514381 A | 5/2005 |
| JP | 2016-520663 A | 7/2016 |
| JP | 2016520663 A | 7/2016 |
| RU | 2510396 C2 | 3/2014 |
| WO | 1996004900 A1 | 2/1996 |
| WO | 1996004901 A1 | 2/1996 |
| WO | 1999002497 A2 | 1/1999 |
| WO | 2000020001 A1 | 4/2000 |
| WO | 2001001972 A2 | 1/2001 |
| WO | 2001070731 A1 | 9/2001 |
| WO | WO 2001/066113 A1 | 9/2001 |
| WO | 2002/064213 A1 | 8/2002 |
| WO | 2002094795 A1 | 11/2002 |
| WO | 2003047517 A2 | 6/2003 |
| WO | 2003047581 A1 | 6/2003 |
| WO | 2003048123 A1 | 6/2003 |
| WO | 2004024150 A2 | 3/2004 |
| WO | 2006/089494 A1 | 8/2006 |
| WO | 2010015628 A1 | 2/2010 |
| WO | 2010015655 A1 | 2/2010 |
| WO | 2010018154 A1 | 2/2010 |
| WO | 2010048095 A2 | 4/2010 |
| WO | 2011092290 A1 | 8/2011 |
| WO | 2011092293 A2 | 8/2011 |
| WO | 2011095450 A1 | 8/2011 |
| WO | 2012/117073 A2 | 9/2012 |
| WO | 2012139876 A1 | 10/2012 |
| WO | 2013188465 A2 | 12/2013 |
| WO | 2014018468 A1 | 1/2014 |
| WO | WO 2014/199316 A1 | 12/2014 |
| WO | 2015/197079 A1 | 12/2015 |
| WO | 2017021438 A1 | 2/2017 |
| WO | 2019025931 A1 | 2/2019 |
| WO | 2020157640 A1 | 8/2020 |

OTHER PUBLICATIONS

Keck et al., "Fenobam sulfate inhibits cocaine-taking and cocaine-seeking behavior in rats: implications for addiction treatment in humans," Psychopharmacology. 22:253-65 (2013).
International Search Report dated Nov. 6, 2018 for PCT International Application No. PCT/IB2018/055664 (3 pages).
M. F. Olive et al: "The mGluR5 Antagonist 6-Methyl-2-(phenylethynyl)pyridine Decreases Ethanol Consumption via a Protein Kinase C-Dependent Mechanism", Molecular Pharmacology, vol. 67, No. 2, 2005, pp. 349-355, (2004).
Keck Thomas et al., "Fenobam sulfate inhibits cocaine-taking and cocaine-seeking behavior in rats: implications for addiction treatment in humans", Psychopharmacology, 229:253-265, (2013).
Keek et al.: "Fenobam sulfate inhibits cocaine-taking and cocaine seeking behavior in rats: implications for addiction treatment in humans" Psychopharmacology, 2013, vol. 229, p. 253-265.
Wang et al.: "Role of mGluR5 Neurotransmission in Reinstated Cocaine seeking", Addict Biol., 2013, vol. 18, No. 1, p. 40-49.
Office Action in corresponding JP application 2020-502952 dated Jan. 24, 2023 (pp. 1-3) and english translation thereof.
Wang, X., et al., "Role of mGluR5 Neurotransmission in Reinstated Cocaine-seeking", Addict Biol, Jan. 2013, vol. 18, No. 1, pp. 40-49.
Masanari Kunimoto; English translation of Abstract "Mechanism of itching in the peripheral nervous system" Journal of Clinical and Medicine Experimental (Igaku No Ayumi), May 26, 2001, vol. 197, No. 8, pp. 591-594.
Awad et al: "Activation of Metabotropic Glutamate Receptor 5 Has Direct Excitatory Effects and Potentiates NMDA Receptor Currents in Neurons of the Subthalamic Nucleus" The Journal of Neuroscience, Nov. 1, 2000, 20(21):7871-7879.
Benquet-et al: "Two Distinct Signaling Pathways Upregulate NMDA Receptor Responses via Two Distinct Metabotropic Glutamate Receptor Subtypes" The Journal of Neuroscience, Nov. 15, 2002, 22(22):9679-9686.
Cosoff et al; "The prevalence of comorbid anxiety in schizophrenia, schizoaffective disorder and bipolar disorder"; Australian and New Zealand Journal of Psychiatry 1998; 32:67-72.
Fretwell_et al; "Palladium Catalysed Tandem Cyclisation—Anion Capture Processes. Part 4: Organotin(IV) Transfer Agents" Tetrahedron 56 (2000) 7525-7539.
Henry_et al; "The mGluR5 antagonist MPEP, but not the mGluR2/3 agonist LY314582, augments PCP effects on prepulse inhibition and locomotor activity", Neuropharmacology 43 (2002) 1199-1209.
Labbate et al;"Panic Disorder in Schizophrenia" Can J Psychiatry 1999;44 :488-490.
Mannaioni et al;"Metabotropic Glutamate Receptors 1 and 5 Differentially Regulate CA1 Pyramidal Cell Function", The Journal of Neuroscience, Aug. 15, 2001, 21(16):5925-5934.
Pisani-et al."METABOTROPIC Glutamate Receptor 5 Mediates the Potentiation of N-Methyl-D-Aspartate Responses in Medium Spiny Striatal Neurons", Neuroscience vol. 106, No. 3, pp. 579587, 2001.
Spooren-et al.; "Novel allosteric antagonists shed light on mglu(5) receptors and CNS disorders", Trends Pharmacol Sci. Jul. 2001;22(7):331-7. doi: 10.1016/s0165-6147(00)01694-1.
Kerper et al; "Persistence of Psychological Distress in Surgical Patients with Interest in Psychotherapy: Results of a 6-Month Follow-Up" PLOS ONE | Dec. 2012 | vol. 7 | Issue 12 | e51167 (pp. 1-9).
Lindsley et al_:"Recent progress in the discovery and development of negative allosteric modulators of mGluR5", Current Opinion in Drug Discovery & Development 2009 12(4):446-457, ISSN 2040-3437.
Nokhodchi et al; "The Role of Oral Controlled Release Matrix Tablets in Drug Delivery Systems"; BioImpacts, 2012, 2(4), 175-187, doi: 10.5681/bi.2012.027.
Kozela et al;"Inhibitory effects of MPEP, an mGluR5 antagonist, and memantine, an N-methyl-D-aspartate receptor antagonist, on morphine antinociceptive tolerance in mice" Psychopharmacology (Berl). Jan. 2003;165(3):245-51. doi: 10.1007/s00213-002-1287-8. Epub Nov. 20, 2002.
Smith et al; "Effects of mGlu1 and mGlu5 metabotropic glutamate antagonists to reverse morphine tolerance in mice" Eur J Pharmacol May 25, 2004:492(2-3):137-42. doi: 10.1016/j.ejphar.2004.03.055.
Xu et al."Role of spinal metabotropic glutamate receptor subtype 5 in the development of tolerance to morphine-induced antinociception in rat" Neurosci Lett Jun. 13, 2007;420(2):155-9. doi: 10.1016/j.neulet.2007.04.065. Epub May 3, 2007.
Osikowicz et al; "Glutamate receptor ligands attenuate allodynia and hyperalgesia and potentiate morphine effects in a mouse model of neuropathic pain" Pain, vol. 139, Issue 1, Sep. 30, 2008, pp. 117-126.
Lee et al_; "Pharmacological Profiles of Oligomerized μ-Opioid Receptors" Cells. Dec. 2013; 2(4): 689-714. Published online Oct. 11, 2013. doi: 10.3390/cells2040689.
Gass et al.; "Role of protein kinase C epsilon (PKCε) in the reduction of ethanol reinforcement due to mGluR5 antagonism in the nucleus accumbens shell" Psychopharmacology (2009) 204:587-597 DOI 10.1007/s00213-009-1490-y.
Fedoseeva ED., Modern Medical Encyclopedia, Norint, 2001 pp. 362-365 (English translation).
Wang et al: "Role of mGluR5 neurotransmission in reinstated cocaine-seeking" Addict Biol. Jan. 2013;18(1):40-9. doi: 10.1111/j.1369-1600.2011.00432.x. Epub Feb. 17, 2012. DOI: 10.1111/i.1369-1600.2011.00432.x.

(56) References Cited

OTHER PUBLICATIONS

Amidon et al., "A theoretical basis for a biopharmaceutic drug classification: the correlation of in vitro drug product dissolution and in vivo bioavailability", Pharm Res, Mar. 1995;12(3):413-20. doi: 10.1023/a:1016212804288.

Backstrom et al., "mGluR5 antagonist MPEP reduces ethanol-seeking and relapse behavior", Neuropsychopharmacology, May 2004;29(5):921-8. doi: 10.1038/sj.npp.1300381.

Bastin et al, "Salt Selection and Optimisation Procedures for Pharmaceutical New Chemical Entities" Org. Proc. Res. Dev. 2000, 4, 5, 427-435, doi.org/10.1021/op000018u.

Chou; "Drug Combination Studies and Their Synergy Quantification Using the Chou-Talalay Method" Cancer Res; 70(2) Jan. 15, 2010, doi: 10.1158/0008-5472.CAN-09-1947.

Gass et al; "mGluR5 antagonism attenuates methamphetamine reinforcement and prevents reinstatement of methamphetamine seeking behavior in rats", Neuropsychopharmacology. Mar. 2009 ; 34(4): 820-833. doi:10.1038/npp.2008.140.

Harpsoe et al; "Selective Negative Allosteric Modulation of Metabotropic Glutamate Receptors—A Structural Perspective of Ligands and Mutants"_Sep. 11, 2015_Scientific Reports, 5:13869 (2015).

Kocbek et al;, "Preparation and evaluation of nanosuspensions for enhancing the dissolution of poorly soluble drugs"; International Journal of Pharmaceutics 312 (2006) 179-186.

Levenga et al; "AFQ056, a new mGluR5 antagonist for treatment of fragile X syndrome", Neurobiol Dis. Jun. 2011;42(3):311-7. doi: 10.1016/j.nbd.2011.01.022. Epub Feb. 21, 2011.

Mcgeehan et al; "The mGluR5 antagonist MPEP reduces the conditioned rewarding effects of cocaine but not other drugs of abuse" Synapse Mar. 2003;47(3):240-2. doi: 10.1002/syn.10166.

SAMSHA publication: Medication for the Treatment of Alcohol Use Disorder_ A Brief Guide_ 2015, pp. 1-39.

Moos et al; "Rates and predictors of relapse after natural and treated remission from alcohol use disorders" Addiction. Feb. 2006 ; 101(2): 212-222.

Osborne et al; "A Role for mGluR5 Receptors in Intravenous Methamphetamine Self-Administration" Ann. N.Y. Acad. Sci. 1139: 206-211 (2008). 2008 New York Academy of Sciences. doi: 10.1196/annals.1432.034.

Petzold et al; "Targeting mGlu5 for Methamphetamine Use Disorder" Pharmacology & Therapeutics 224 (2021) 107831.

Rehm; "The risks associated with alcohol use and alcoholism" Alcohol Res Health. 2011;34(2):135-43.

Rodriguez Parkitna et al; "Novelty-Seeking Behaviors and the Escalation of Alcohol Drinking After Abstinence in Mice Are Controlled by Metabotropic Glutamate Receptor 5 on Neurons Expressing Dopamine D1 Receptors" Biol Psychiatry 2013;73:263-270.

Kitagawa_2012_Pharmacology Textbook ISBN978-4-7598-1620-4 (pp. 1-9).

Office Action in corresponding CN application No. 202080008828.5 dated Jul. 18, 2023 (pp. 1-7) and english translation thereof (pp. 1-8).

\* cited by examiner

USE OF MAVOGLURANT IN THE REDUCTION OF COCAINE USE OR IN PREVENTING RELAPSE INTO COCAINE USE

RELATED APPLICATIONS

This application is a U.S. National Phase filing of International Application Serial No. PCT/IB2018/055664 filed 30 Jul. 2018 and claims priority to U.S. Provisional Application Ser. No. 62/539,003 filed 31 Jul. 2017 all of which are incorporated in their entireties herein.

The present invention relates to uses of a mGluR5 antagonist.

FIELD OF THE INVENTION

The invention relates to the use of the mGluR5 antagonist named mavoglurant, or a pharmaceutically acceptable salt thereof, in the reduction of cocaine use by a cocaine use disorder patient; in preventing relapse into cocaine use by a cocaine use disorder patient; in the promotion of cocaine abstinence by a cocaine use disorder patient; in the treatment of the symptoms of depression or anxiety associated with cocaine use disorder. In particular, it relates to the use of mavoglurant, or a pharmaceutically acceptable salt thereof, in the reduction of cocaine use/in preventing relapse into cocaine use, by a cocaine use disorder patient.

BACKGROUND OF THE INVENTION

Cocaine use disorder is a complex psychiatric disorder, defined with reference to DSM-5 criteria (i.e. according to the Diagnostic and Statistical Manual of Mental Disorders. 5$^{th}$ Edition, Washington, D.C.: American Psychiatric Association, 2013), which continues to grow into a significant worldwide health problem having adverse medical, social and economic effects (D. Shorter et al., *Expert Opin. Emerging Drugs*, 20(1), 2015). Socio-economic dangers associated with cocaine use include increased crime and violence. Adverse medical consequences derived from the use of cocaine are, for example, but not limited to, cardiovascular disorders (e.g. hypertension, stroke, heart attack, cardiac arrhythmias, cardiomyopathy), gastrointestinal disorders, respiratory disorders (e.g. bronchitis, chest pain) convulsive seizures, psychomotor agitation, sleep disorders and psychosis. Cocaine use also affects areas of the brain related to cognition (e.g. memory, learning, attention). Further associated health risks include infectious diseases (e.g. hepatitis B and C or HIV), and, indeed, any route of cocaine administration can lead into serious medical emergencies that can ultimately result in death. In addition, it is common that cocaine use disorder patients present comorbidity with psychiatric disorders.

The complete biological mechanism of cocaine dependence is not fully understood, yet. Thus, pharmacological treatment of cocaine use disorder has focused on the various stages a cocaine use disorder patient may go through and thus it has aimed to target different aspects, for example: i) attenuate the rewarding effects of cocaine use (e.g. euphoric effects), ii) act as a "substitution treatment" for cocaine, iii) alleviate cocaine withdrawal symptoms (e.g. cocaine craving, anxiety or depression), D. Shorter et al., *Expert Opin. Emerging Drugs*, 20(1), 2015. Most promising results have been obtained with desipramine and amantadine, which have shown to alleviate symptoms of cocaine withdrawal. In particular, desipramine has been shown to reduce both cocaine use and cocaine craving, although the reduction in craving developed only slowly (i.e. over 7 to 14 days), which made frequent the relapse into cocaine use. Other pharmacological agents that have been tested include GABA agents (e.g. topiramate, tiagabine, baclofen and vigabatrin), agonist replacement agents (e.g. modafinil, methylphenidate, methadone, buprenorphine), dopamine agents (such as bupropion, the combination of levodopa with carbidopa, risperidone, olanzapine, aripiprazole, dextroamphetamine), D3 receptor ligands (e.g. CJB090), corticotropin-releasing factor (CRF) receptor antagonists (e.g. CP154,526), cannabinoid CR1 receptor antagonists, dual dopamine-serotonin releasers (e.g. PAL-287), noradregenic agents (e.g. doxazosin, disulfiram, nepicastat), 5-HT$_{1A}$ receptor partial agonists (e.g. buspirone), MU opiod agonists (buprenorophine), desipramine and amantadine. However, despite the many research efforts in this field, which have included over a hundred clinical trials, currently, no medications for treatment have been approved by regulatory authorities (*Pharmacol Rev* 68:533-562, July 2016; *International Journal of Neuropsychopharmacology*, 11, 425-438, 2008). In addition, clinical treatments for cocaine use disorder patients are complicated by the high propensity of these patients not to complete the treatment and to relapse.

Cocaine is one the most addictive substance of abuse due to its immediate and powerful rewarding effects (e.g. feelings of euphoria and increased energy). Cocaine users often increase their dose aiming at increasing and extending the rewarding effects of cocaine. Withdrawal from cocaine use is associated with adverse symptoms, for example, among others, anxiety, depression, pain (e.g. headache) and cocaine craving. Oftentimes the severe discomfort caused by cocaine's abstinence may prompt patients to return to the use of cocaine in an attempt to alleviate the withdrawal symptoms. Finding pharmacotherapies for the treatment of cocaine use disorder is a great challenge and a high medical need, in particular, the finding of medications that can help achieve or maintain abstinence from the use of cocaine.

Preclinical models have shown that other mGluR5 antagonists, such as MPEP [i.e. 2-methyl-6-(2-phenylethynyl)pyridine] and MTEP [i.e. 3-[2-(2-methylthiazol-4-yl) ethynyl]pyridine] decreased cocaine self-administration in mice (e.g. in Chiamulera, C. et al., *Nat. Neurosci.* 2001, 4, 873-874) or decreased cocaine self-administration in rats (e.g. in Kenny, P. J. et al., *Behav. Pharmacol.* 14, S55; Martin-Fardon R., et al., *J. Pharmacol Exp Ther* 2009, 329(3): 1084). However, neither MTEP nor MPEP have been further developed due to their shortcomings as therapeutic agents (Keck et al., 2013, *Psychopharmacology*, 229 (2): 253-65): MTEP shows, for example, potent inhibition of cytochrome P450 1A2 and a rapid metabolism (Smith et al. 2004, *Bioorg Med Chem Lett* 14:5481-5484) and MPEP shows, for example, off-target effects on NMDA receptors, monoamine oxidase, and the norepinephrine transporter (Cosford et al., *J. Med. Chem.*, 2003, 46 (2), pp 204-206; O'Leary et al., 2000, *Br J Pharmacol* 131:1429-1437; Heidbreder et al., 2003, *Synapse* 50:269-276; Lea and Faden, 2006 *CNS Drug Rev* 12:149-166).

It has been found that mavoglurant may be an ideal candidate for treating patients diagnosed with cocaine use disorder, having therapeutic advantages for said patient population, such as one or more of the following:

i) it promotes cocaine abstinence, for example, compared to placebo, for example by maintaining abstinence or by reducing the amount or frequency of cocaine use, for example as assessed by urinalysis (e.g. by measuring metabolites of cocaine in urine, such as benzoylecgonine) or as assessed by using self-reported cocaine use with standardized tools like the Timeline Follow-Back self-report [Sobell, L. C., Sobell, M. B. (1996) Timeline Followback User's Guide: A Calendar Method for Assessing Alcohol and Drug Use. Addiction Research Foundation, Toronto, Ontario, Canada; *J. Anal. Toxicolo.*, 2002, 26: 393-400];

ii) it decreases relapse into cocaine use, for example, compared to placebo, for example it increases the time to relapse or the rates of patient relapse in a treatment program, such as a clinical trial;

iii) it alleviates (e.g. by eliminating or by reducing intensity, duration or frequency), for example compared to placebo, one or more of symptoms associated with cocaine use disorder selected from:
  a. depressive symptoms, for example as assessed from the Beck's Depression Inventory [Beck, A. T. et al., (1961) An inventory for measuring depression. *Archives of General Psychiatry*, 4, 561-571; Beck, A. T. et al., (1988) Psychometric properties of the Beck Depression Inventory: Twenty-five years of evaluation. *Clinical Psychology Review*, 8(1), 77-100]; and
  b. anxiety symptoms, for example as assessed from the State-Trait Anxiety Inventory [Spielberger, C. D. (1989). *State-Trait Anxiety Inventory: Bibliography* (2$^{nd}$ Ed.). Palo Alto, Calif.: Consulting Psychologists Press; Spielberger, C. D. et al., (1983). *Manual for the State-Trait Anxiety Inventory*. Palo Alto, Calif.: Consulting Psychologists Press].

iv) it increases retention of patients in treatment, for example, compared to placebo, for example it increases the rates of patient retention in a treatment program, such as a clinical trial (e.g. as measured by patient attendance at scheduled clinic visits and/or time to dropout from clinical protocol);

v) it improves global functioning, for example as assessed from the Clinical Global Impression Scale-Severity (CGI-S) and Improvement (CGI-1) (Psychiatry, 2007, 4(7): 28-37)

vi) it has a favorable therapeutic profile, such as a favorable safety profile or metabolic profile, for example a favorable profile in relation to psychiatric adverse events, genotoxicity, or cardiovascular adverse events (e.g. blood pressure, heart rate, electrocardiography parameters); for example, it has better therapeutic profile (e.g. fewer side effects, decreased off-target effects or decreased toxicity, such as decreased genotoxicity) compared to known therapeutic agent/s that have shown efficacy in the treatment of cocaine use disorder; or vii) it has one or more of therapeutic advantages i) to vi), as listed here above, and it also reduces alcohol use, for example, compared to placebo, for example by reducing the amount or frequency of alcohol use, for example as assessed by urinalysis (e.g. measuring metabolites of alcohol, such as ethyl glucuronide) or as assessed by using self-reported alcohol use with standardized tools like the Timeline Follow-Back self-report (*J. Anal. Toxicolo* 2002, 26: 393-400).

SUMMARY OF THE INVENTION

The invention relates to the use of mavoglurant, or a pharmaceutically acceptable salt thereof:
in the reduction of cocaine use by a cocaine use disorder patient;
in preventing relapse into cocaine use by a cocaine use disorder patient;
in the promotion of cocaine abstinence by a cocaine use disorder patient;
in the treatment of the symptoms of depression or anxiety associated with cocaine use disorder.

DETAILED DESCRIPTION OF THE INVENTION

Figure 1:
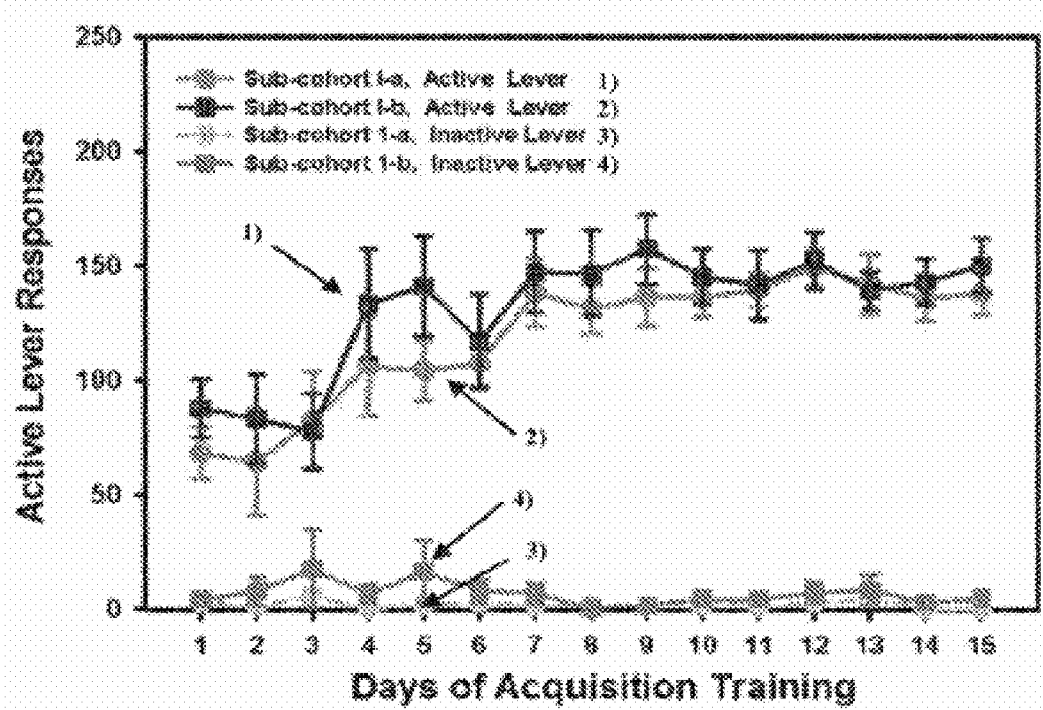
FIG. 1: Cocaine (0.3 mg/kg/infusion, FR5) self-administration learning curves in Phase I. Data represent the means+SEM. N=12 per treatment group.
Figure 2:
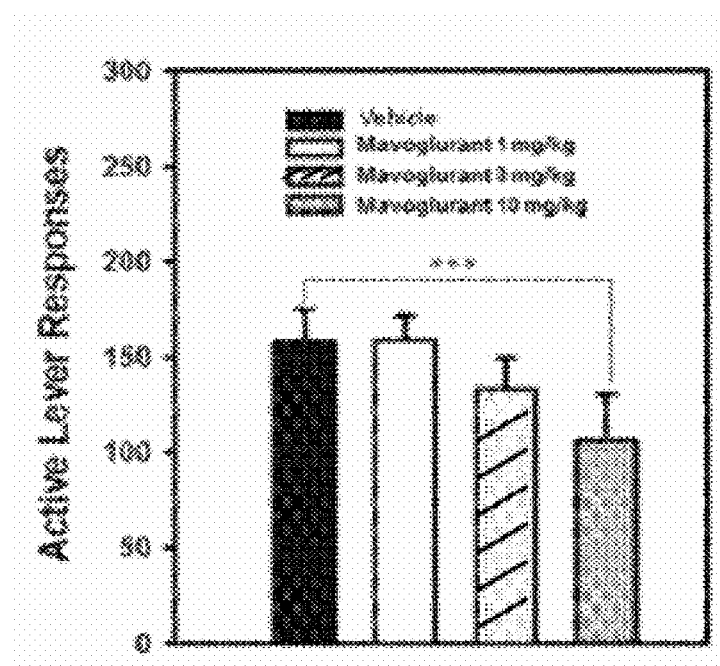
FIG. 2: Acute effects of mavoglurant on cocaine self-administration in two sub-cohorts of rats. Data are presented as mean+SEM. Asterisks (***: $P<0.001$) indicate significant differences compared to saline or vehicle treatment. N=12 per treatment group.

Embodiments of the present invention are:

Embodiments (a)

1a. Mavoglurant, or a pharmaceutically acceptable salt thereof, for use in the reduction of cocaine use by a cocaine use disorder patient.

2a. Mavoglurant, or a pharmaceutically acceptable salt thereof, for use in preventing relapse into cocaine use by a cocaine use disorder patient.

3a. Mavoglurant, or a pharmaceutically acceptable salt thereof, for use in the promotion of cocaine abstinence by a cocaine use disorder patient.

4a. Mavoglurant, or a pharmaceutically acceptable salt thereof, for use in the treatment of the symptoms of depression or anxiety associated with cocaine use disorder.

5a. Mavoglurant, or a pharmaceutically acceptable salt thereof, for use according to any one of embodiments 1a to 4a, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

6a. Mavoglurant, or a pharmaceutically acceptable salt thereof, for use according to any one of embodiments 1a to 5a, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7a. Mavoglurant, or a pharmaceutically acceptable salt thereof, for use according to any one of embodiments 1a to 6a, wherein the use is combined with standardized psychological treatment, for example, at individual or group level.

8a. Mavoglurant, or a pharmaceutically acceptable salt thereof, for use according to any one of embodiments 1a to 7a, wherein the use is combined with psychosocial or behavioral therapy or combination thereof, in particular contingency management based therapy.

9a. Mavoglurant, or a pharmaceutically acceptable salt thereof, for use according to embodiment 8a, wherein the psychosocial or the behavioral therapy is computer-assisted.

10a. Mavoglurant, or a pharmaceutically acceptable salt thereof, for use according to any one of embodiments 1a to 9a, wherein the use is concomitant with methadone or buprenorphine treatment.

11a. Mavoglurant, or a pharmaceutically acceptable salt thereof, for use according to any one of embodiments 1a to 10a, wherein mavoglurant, or a pharmaceutically acceptable salt thereof, is administered in combination with a further active agent.

12a. Mavoglurant, or a pharmaceutically acceptable salt thereof, for use according to embodiment 11a, wherein the further active agent is selected from a GABA agent (such as topiramate, baclofen or tiagabine) or a dopamine agent (such as bupropion, the combination of L-dopa and carbidopa).

13a. Mavoglurant, or a pharmaceutically acceptable salt thereof, for use according to any one of embodiments 1a to 12a, wherein the patient has a genetic variation associated with a substance use disorder, such as a genetic variation associated with cocaine use disorder.

14a. Mavoglurant, or a pharmaceutically acceptable salt thereof, for use according to any one of embodiments 1a to 13a, wherein mavoglurant, or a pharmaceutically acceptable salt thereof, is administered in an immediate-release form or a modified-release form.

15a. Mavoglurant, or a pharmaceutically acceptable salt thereof, for use according to any one of embodiments 1a to 14a, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16a. Mavoglurant, or a pharmaceutically acceptable salt thereof, for use according to embodiment 15a, wherein mavoglurant, or a pharmaceutically acceptable salt thereof, is administered with food.

17a. Mavoglurant, or a pharmaceutically acceptable salt thereof, for use according to embodiment 15a or 16a, wherein mavoglurant, or a pharmaceutically acceptable salt thereof, is administered in the morning and in the evening separated by a 12 hour interval.

18a. Mavoglurant, or a pharmaceutically acceptable salt thereof, for use according to any of the preceding embodiments, wherein cocaine use disorder is associated with binge drinking.

Embodiments (b)

1b. A pharmaceutical composition comprising mavoglurant, or a pharmaceutically acceptable salt thereof, and at least one pharmaceutically acceptable excipient, for use in the reduction of cocaine use by a cocaine use disorder patient.

2b. A pharmaceutical composition comprising mavoglurant, or a pharmaceutically acceptable salt thereof, and at least one pharmaceutically acceptable excipient, for use in preventing relapse into cocaine use by a cocaine use disorder patient.

3b. A pharmaceutical composition comprising mavoglurant, or a pharmaceutically acceptable salt thereof, and at least one pharmaceutically acceptable excipient, for use in the promotion of cocaine abstinence by a cocaine use disorder patient.

4b. A pharmaceutical composition comprising mavoglurant, or a pharmaceutically acceptable salt thereof, and at least one pharmaceutically acceptable excipient, for use in the treatment of the symptoms of depression or anxiety associated with cocaine use disorder.

5b. A pharmaceutical composition comprising mavoglurant, or a pharmaceutically acceptable salt thereof, and at least one pharmaceutically acceptable excipient, for use according to any one of embodiments 1b to 4b, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

6b. A pharmaceutical composition comprising mavoglurant, or a pharmaceutically acceptable salt thereof, and at least one pharmaceutically acceptable excipient, for use according to any one of embodiments 1 b to 5b, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7b. A pharmaceutical composition comprising mavoglurant, or a pharmaceutically acceptable salt thereof, and at least one pharmaceutically acceptable excipient, for use according to any one of embodiments 1b to 6b, wherein the use is combined with standardized psychological treatment, for example, at individual or group level.

8b. A pharmaceutical composition comprising mavoglurant, or a pharmaceutically acceptable salt thereof, and at least one pharmaceutically acceptable excipient, for use according to any one of embodiments 1b to 7b, wherein the use is combined with psychosocial or behavioral therapy or combination thereof, in particular contingency management based therapy.

9b. A pharmaceutical composition comprising mavoglurant, or a pharmaceutically acceptable salt thereof, and at least one pharmaceutically acceptable excipient, for use according to embodiment 8b, wherein the psychosocial or the behavioral therapy is computer-assisted.

10b. A pharmaceutical composition comprising mavoglurant, or a pharmaceutically acceptable salt thereof, and at least one pharmaceutically acceptable excipient, for use according to any one of embodiments 1b to 9b, wherein the use is concomitant with methadone or buprenorphine treatment.

11b. A pharmaceutical composition comprising mavoglurant, or a pharmaceutically acceptable salt thereof, and at least one pharmaceutically acceptable excipient, for use according to any one of embodiments 1b to 10b, wherein mavoglurant, or a pharmaceutically acceptable salt thereof, is administered in combination with a further active agent.

12b. A pharmaceutical composition comprising mavoglurant, or a pharmaceutically acceptable salt thereof, and at least one pharmaceutically acceptable excipient, for use according to embodiment 11b, wherein the further active agent is selected from a GABA agent (such as topiramate, baclofen or tiagabine) or a dopamine agent (such as bupropion, the combination of L-dopa and carbidopa).

13b. A pharmaceutical composition comprising mavoglurant, or a pharmaceutically acceptable salt thereof, and at least one pharmaceutically acceptable excipient, for use according to any one of embodiments 1 b to 12b, wherein the patient has a genetic variation associated with a substance use disorder, such as a genetic variation associated with cocaine use disorder.

14b. A pharmaceutical composition comprising mavoglurant, or a pharmaceutically acceptable salt thereof, and at least one pharmaceutically acceptable excipient, for use according to any one of embodiments 1 b to 13b, which is an immediate-release form or a modified-release form.

15b. A pharmaceutical composition comprising mavoglurant, or a pharmaceutically acceptable salt thereof, and at least one pharmaceutically acceptable excipient, for use according to any one of embodiments 1 b to 14b, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16b. A pharmaceutical composition comprising mavoglurant, or a pharmaceutically acceptable salt thereof, and at least one pharmaceutically acceptable excipient, for use according to embodiment 15b, wherein mavoglurant, or a pharmaceutically acceptable salt thereof, is administered with food.

17b. A pharmaceutical composition comprising mavoglurant, or a pharmaceutically acceptable salt thereof, and at least one pharmaceutically acceptable excipient, for use according to embodiment 15b or 16b, wherein mavoglurant, or a pharmaceutically acceptable salt thereof, is administered in the morning and in the evening separated by a 12 hour interval.

18b. A pharmaceutical composition comprising mavoglurant, or a pharmaceutically acceptable salt thereof, and at least one pharmaceutically acceptable excipient, for use according to any of the preceding embodiments, wherein cocaine use disorder is associated with binge drinking.

Embodiments (c)

1c. A pharmaceutical combination comprising mavoglurant, or a pharmaceutically acceptable salt thereof, and at least one further pharmaceutical active ingredient, for use in the reduction of cocaine use by a cocaine use disorder patient.

2c. A pharmaceutical combination comprising mavoglurant, or a pharmaceutically acceptable salt thereof, and at least one further pharmaceutical active ingredient, for use in preventing relapse into cocaine use by a cocaine use disorder patient.

3c. A pharmaceutical combination comprising mavoglurant, or a pharmaceutically acceptable salt thereof, and at least one further pharmaceutical active ingredient, for use in the promotion of cocaine abstinence by a cocaine use disorder patient.

4c. A pharmaceutical combination comprising mavoglurant, or a pharmaceutically acceptable salt thereof, and at least one further pharmaceutical active ingredient, for use in the treatment of the symptoms of depression or anxiety associated with cocaine use disorder.

5c. A pharmaceutical combination comprising mavoglurant, or a pharmaceutically acceptable salt thereof, and at least one further pharmaceutical active ingredient, for use according to any one of embodiments 1c to 4c, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

6c. A pharmaceutical combination comprising mavoglurant, or a pharmaceutically acceptable salt thereof, and at least one further pharmaceutical active ingredient, for use according to any one of embodiments 1c to 5c, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7c. A pharmaceutical combination comprising mavoglurant, or a pharmaceutically acceptable salt thereof, and at least one further pharmaceutical active ingredient, for use according to any one of embodiments 1c to 6c, wherein the use is combined with standardized psychological treatment, for example, at individual or group level.

8c. A pharmaceutical combination comprising mavoglurant, or a pharmaceutically acceptable salt thereof, and at least one further pharmaceutical active ingredient, for use according to any one of embodiments 1c to 7c, wherein the use is combined with psychosocial or behavioral therapy or combination thereof, in particular contingency management based therapy.

9c. A pharmaceutical combination comprising mavoglurant, or a pharmaceutically acceptable salt thereof, and at least one further pharmaceutical active ingredient, for use according to embodiment 8c, wherein the psychosocial or the behavioral therapy is computer-assisted.

10c. A pharmaceutical combination comprising mavoglurant, or a pharmaceutically acceptable salt thereof, and at least one further pharmaceutical active ingredient, for use according to any one of embodiments 1c to 9c, wherein the use is concomitant with methadone or buprenorphine treatment.

11c. A pharmaceutical combination comprising mavoglurant, or a pharmaceutically acceptable salt thereof, and at least one further pharmaceutical active ingredient, for use according to any one of embodiments 1c to 10c, wherein the further active agent is selected from a GABA agent (such as topiramate, baclofen or tiagabine) or a dopamine agent (such as bupropion, the combination of L-dopa and carbidopa).

12c. A pharmaceutical combination comprising mavoglurant, or a pharmaceutically acceptable salt thereof, and at least one further pharmaceutical active ingredient, for use according to any one of embodiments 1c to 11c, wherein the patient has a genetic variation associated with a substance use disorder, such as a genetic variation associated with cocaine use disorder.

13c. A pharmaceutical combination comprising mavoglurant, or a pharmaceutically acceptable salt thereof, and at least one further pharmaceutical active ingredient, for use according to any one of embodiments 1c to 12c, wherein mavoglurant, or a pharmaceutically acceptable salt thereof, is administered in an immediate-release form or a modified-release form.

14c. A pharmaceutical combination comprising mavoglurant, or a pharmaceutically acceptable salt thereof, and at least one further pharmaceutical active ingredient, for use according to any one of embodiments 1c to 13c, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

15c. A pharmaceutical combination comprising mavoglurant, or a pharmaceutically acceptable salt thereof, and at least one further pharmaceutical active ingredient, for use according to embodiment 14c, wherein mavoglurant, or a pharmaceutically acceptable salt thereof, is administered with food.

16c. A pharmaceutical combination comprising mavoglurant, or a pharmaceutically acceptable salt thereof, and at least one further pharmaceutical active ingredient, for use according to embodiment 14c or 15c, wherein mavoglurant, or a pharmaceutically acceptable salt thereof, is administered in the morning and in the evening separated by a 12 hour interval.

17c. A pharmaceutical combination comprising mavoglurant, or a pharmaceutically acceptable salt thereof, and at least one further pharmaceutical active ingredient, for use according to any of the preceding embodiments, wherein cocaine use disorder is associated with binge drinking.

Embodiments (d)

1d. Use of mavoglurant, or a pharmaceutically acceptable salt thereof, for the manufacture of a medicament for the reduction of cocaine use by a cocaine use disorder patient.

2d. Use of mavoglurant, or a pharmaceutically acceptable salt thereof, for the manufacture of a medicament for preventing relapse into cocaine use by a cocaine use disorder patient.

3d. Use of mavoglurant, or a pharmaceutically acceptable salt thereof, for the manufacture of a medicament for the promotion of cocaine abstinence by a cocaine use disorder patient.

4d. Use of mavoglurant, or a pharmaceutically acceptable salt thereof, for the manufacture of a medicament for the treatment of the symptoms of depression or anxiety associated with cocaine use disorder.

5d. Use of mavoglurant, or a pharmaceutically acceptable salt thereof, according to any one of embodiments 1d to 4d, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

6d. Use of mavoglurant, or a pharmaceutically acceptable salt thereof, according to any one of embodiments 1d to 5d, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7d. Use of mavoglurant, or a pharmaceutically acceptable salt thereof, according to any one of embodiments 1d to 6d, wherein the use is combined with standardized psychological treatment, for example, at individual or group level.

8d. Use of mavoglurant, or a pharmaceutically acceptable salt thereof, according to any one of embodiments 1d to 7d, wherein the use is combined with psychosocial or behavioral therapy or combination thereof, in particular contingency management based therapy.

9d. Use of mavoglurant, or a pharmaceutically acceptable salt thereof, according to embodiment 8d, wherein the psychosocial or the behavioral therapy is computer-assisted.

10d. Use of mavoglurant, or a pharmaceutically acceptable salt thereof, according to any one of embodiments 1d to 9d, wherein the use is concomitant with methadone or buprenorphine treatment.

11d. Use of mavoglurant, or a pharmaceutically acceptable salt thereof, according to any one of embodiments 1d to 10d, wherein mavoglurant, or a pharmaceutically acceptable salt thereof, is administered in combination with a further active agent.

12d. Use of mavoglurant, or a pharmaceutically acceptable salt thereof, according to embodiment 11d, wherein the further active agent is selected from a GABA agent (such as topiramate, baclofen or tiagabine) or a dopamine agent (such as bupropion, the combination of L-dopa and carbidopa).

13d. Use of mavoglurant, or a pharmaceutically acceptable salt thereof, according to any one of embodiments 1d to 12d, wherein the patient has a genetic variation associated with a substance use disorder, such as a genetic variation associated with cocaine use disorder.

14d. Use of mavoglurant, or a pharmaceutically acceptable salt thereof, according to any one of embodiments 1d to 13d, wherein mavoglurant, or a pharmaceutically acceptable salt thereof, is administered in an immediate-release form or a modified-release form.

15d. Use of mavoglurant, or a pharmaceutically acceptable salt thereof, according to any one of embodiments 1d to 14d, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16d. Use of mavoglurant, or a pharmaceutically acceptable salt thereof, according to embodiment 15d, wherein mavoglurant, or a pharmaceutically acceptable salt thereof, is administered with food.

17d. Use of mavoglurant, or a pharmaceutically acceptable salt thereof, according to embodiment 15d or 16d, wherein mavoglurant, or a pharmaceutically acceptable salt thereof, is administered in the morning and in the evening separated by a 12 hour interval.

18d. Use of mavoglurant, or a pharmaceutically acceptable salt thereof, according to any of the preceding embodiments, wherein cocaine use disorder is associated with binge drinking.

Embodiments (e)

1e. Use of a pharmaceutical composition comprising mavoglurant, or a pharmaceutically acceptable salt thereof, and at least one pharmaceutically acceptable excipient, for the manufacture of a medicament for the reduction of cocaine use by a cocaine use disorder patient.

2e. Use of a pharmaceutical composition comprising mavoglurant, or a pharmaceutically acceptable salt thereof, and at least one pharmaceutically acceptable excipient, for the manufacture of a medicament for preventing relapse into cocaine use by a cocaine use disorder patient.

3e. Use of a pharmaceutical composition comprising mavoglurant, or a pharmaceutically acceptable salt thereof, and at least one pharmaceutically acceptable excipient, for the manufacture of a medicament for the promotion of cocaine abstinence by a cocaine use disorder patient.

4e. Use of a pharmaceutical composition comprising mavoglurant, or a pharmaceutically acceptable salt thereof, and at least one pharmaceutically acceptable excipient, for the manufacture of a medicament for the treatment of the symptoms of depression or anxiety associated with cocaine use disorder.

5e. Use of a pharmaceutical composition comprising mavoglurant, or a pharmaceutically acceptable salt thereof, and at least one pharmaceutically acceptable excipient, according to any one of embodiments 1e to 4e, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

6e. Use of a pharmaceutical composition comprising mavoglurant, or a pharmaceutically acceptable salt thereof, and at least one pharmaceutically acceptable excipient, according to any one of embodiments 1e to 5e, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7e. Use of a pharmaceutical composition comprising mavoglurant, or a pharmaceutically acceptable salt thereof, and at least one pharmaceutically acceptable excipient, according to any one of embodiments 1e to 6e, wherein the use is combined with standardized psychological treatment, for example, at individual or group level.

8e. Use of a pharmaceutical composition comprising mavoglurant, or a pharmaceutically acceptable salt thereof, and at least one pharmaceutically acceptable excipient, according to any one of embodiments 1e to 7e, wherein the use is combined with psychosocial or behavioral therapy or combination thereof, in particular contingency management based therapy.

9e. Use of a pharmaceutical composition comprising mavoglurant, or a pharmaceutically acceptable salt thereof, and at least one pharmaceutically acceptable excipient, according to embodiment 8e, wherein the psychosocial or the behavioral therapy is computer-assisted.

10e. Use of a pharmaceutical composition comprising mavoglurant, or a pharmaceutically acceptable salt thereof, and at least one pharmaceutically acceptable excipient, according to any one of embodiments 1e to 9e, wherein the use is concomitant with methadone or buprenorphine treatment.

11e. Use of a pharmaceutical composition comprising mavoglurant, or a pharmaceutically acceptable salt thereof, and at least one pharmaceutically acceptable excipient, according to any one of embodiments 1e to 10e, wherein mavoglurant, or a pharmaceutically acceptable salt thereof, is administered in combination with a further active agent.

12e. Use of a pharmaceutical composition comprising mavoglurant, or a pharmaceutically acceptable salt thereof, and at least one pharmaceutically acceptable excipient, according to embodiment 11e, wherein the further active agent is selected from a GABA agent (such as topiramate, baclofen or tiagabine) or a dopamine agent (such as bupropion, the combination of L-dopa and carbidopa).

13e. Use of a pharmaceutical composition comprising mavoglurant, or a pharmaceutically acceptable salt thereof, and at least one pharmaceutically acceptable excipient, according to any one of embodiments 1e to 12e, wherein the patient has a genetic variation associated with a substance use disorder, such as a genetic variation associated with cocaine use disorder.

14e. Use of a pharmaceutical composition comprising mavoglurant, or a pharmaceutically acceptable salt thereof, and at least one pharmaceutically acceptable excipient, according to any one of embodiments 1e to 13e, wherein mavoglurant, or a pharmaceutically acceptable salt thereof, is administered in an immediate-release form or a modified-release form.

15e. Use of a pharmaceutical composition comprising mavoglurant, or a pharmaceutically acceptable salt thereof, and at least one pharmaceutically acceptable excipient, according to any one of embodiments 1e to 14e, wherein mavoglurant, or a pharmaceutically acceptable salt thereof, is administered in an amount of from 50 mg/b.i.d to 200 mg/b.i.d., in particular 50 mg/b.i.d., 100 mg/b.i.d or 200 mg/b.i.d., such as 200 mg/b.i.d.

16e. Use of a pharmaceutical composition comprising mavoglurant, or a pharmaceutically acceptable salt thereof, and at least one pharmaceutically acceptable excipient, according to embodiment 15e, wherein mavoglurant, or a pharmaceutically acceptable salt thereof, is administered with food.

17e. Use of a pharmaceutical composition comprising mavoglurant, or a pharmaceutically acceptable salt thereof, and at least one pharmaceutically acceptable excipient, according to embodiment 15e or 16e, wherein mavoglurant, or a pharmaceutically acceptable salt thereof, is administered in the morning and in the evening separated by a 12 hour interval.

18e. Use of a pharmaceutical composition comprising mavoglurant, or a pharmaceutically acceptable salt thereof, and at least one pharmaceutically acceptable excipient, according to any of the preceding embodiments, wherein cocaine use disorder is associated with binge drinking.

Embodiments (f)

1f. Use of a pharmaceutical combination comprising mavoglurant, or a pharmaceutically acceptable salt thereof, and at least one further pharmaceutical active ingredient, for the manufacture of a medicament for the reduction of cocaine use by a cocaine use disorder patient.

2f. Use of a pharmaceutical combination comprising mavoglurant, or a pharmaceutically acceptable salt thereof, and at least one further pharmaceutical active ingredient, for the manufacture of a medicament for preventing relapse into cocaine use by a cocaine use disorder patient.

3f. Use of a pharmaceutical combination comprising mavoglurant, or a pharmaceutically acceptable salt thereof, and at least one further pharmaceutical active ingredient, for the manufacture of a medicament for the promotion of cocaine abstinence by a cocaine use disorder patient.

4f. Use of a pharmaceutical combination comprising mavoglurant, or a pharmaceutically acceptable salt thereof, and at least one further pharmaceutical active ingredient, for the manufacture of a medicament for the treatment of the symptoms of depression or anxiety associated with cocaine use disorder.

5f. Use of a pharmaceutical combination comprising mavoglurant, or a pharmaceutically acceptable salt thereof, and at least one further pharmaceutical active ingredient, according to any one of embodiments 1f to 4f, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

6f. Use of a pharmaceutical combination comprising mavoglurant, or a pharmaceutically acceptable salt thereof, and at least one further pharmaceutical active ingredient, according to any one of embodiments 1f to 5f, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7f. Use of a pharmaceutical combination comprising mavoglurant, or a pharmaceutically acceptable salt thereof, and at least one further pharmaceutical active ingredient, according to any one of embodiments 1f to 6f, wherein the use is combined with standardized psychological treatment, for example, at individual or group level.

8f. Use of a pharmaceutical combination comprising mavoglurant, or a pharmaceutically acceptable salt thereof, and at least one further pharmaceutical active ingredient, according to any one of embodiments 1f to 7f, wherein the use is combined with psychosocial or behavioral therapy or combination thereof, in particular contingency management based therapy.

9f. Use of a pharmaceutical combination comprising mavoglurant, or a pharmaceutically acceptable salt thereof, and at least one further pharmaceutical active ingredient, according embodiment 8f, wherein the psychosocial or the behavioral therapy is computer-assisted.

10f. Use of a pharmaceutical combination comprising mavoglurant, or a pharmaceutically acceptable salt thereof, and at least one further pharmaceutical active ingredient, according to any one of embodiments 1f to 9f, wherein the use is concomitant with methadone or buprenorphine treatment.

11f. Use of a pharmaceutical combination comprising mavoglurant, or a pharmaceutically acceptable salt thereof, and at least one further pharmaceutical active ingredient, according to any one of embodiments 1f to 10f, wherein the further active agent is selected from a GABA agent (such as topiramate, baclofen or tiagabine) or a dopamine agent (such as bupropion, the combination of L-dopa and carbidopa).

12f. Use of a pharmaceutical combination comprising mavoglurant, or a pharmaceutically acceptable salt thereof, and at least one further pharmaceutical active ingredient, according to any one of embodiments 1f to 11f, wherein the patient has a genetic variation associated with a substance use disorder, such as a genetic variation associated with cocaine use disorder.

13f. Use of a pharmaceutical combination comprising mavoglurant, or a pharmaceutically acceptable salt thereof, and at least one further pharmaceutical active ingredient, according to any one of embodiments 1f to 12f, wherein mavoglurant, or a pharmaceutically acceptable salt thereof, is administered in an immediate-release form or a modified-release form.

14f. Use of a pharmaceutical combination comprising mavoglurant, or a pharmaceutically acceptable salt thereof, and at least one further pharmaceutical active ingredient, according to any one of embodiments 1c to 13c, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

15f. Use of a pharmaceutical combination comprising mavoglurant, or a pharmaceutically acceptable salt thereof, and at least one further pharmaceutical active ingredient, according to embodiment 14f, wherein mavoglurant, or a pharmaceutically acceptable salt thereof, is administered with food.

16f. Use of a pharmaceutical combination comprising mavoglurant, or a pharmaceutically acceptable salt thereof, and at least one further pharmaceutical active ingredient, according to embodiment 14f or 15f, wherein mavoglurant, or a pharmaceutically acceptable salt thereof, is administered in the morning and in the evening separated by a 12 hour interval.

17f. Use of a pharmaceutical combination comprising mavoglurant, or a pharmaceutically acceptable salt thereof, and at least one further pharmaceutical active ingredient, according to any of the preceding embodiments, wherein cocaine use disorder is associated with binge drinking.

Embodiments (g)

1g. A method for the reduction of cocaine use by a cocaine use disorder patient, in need thereof, comprising administering to said cocaine use disorder patient an effective amount of mavoglurant, or a pharmaceutically acceptable salt thereof.

2g. A method for preventing relapse into cocaine use by a cocaine use disorder patient, in need thereof, comprising administering to said cocaine use disorder patient an effective amount of mavoglurant, or a pharmaceutically acceptable salt thereof.

3g. A method for the promotion of cocaine abstinence by a cocaine use disorder patient, in need thereof, comprising administering to said cocaine use disorder patient an effective amount of mavoglurant, or a pharmaceutically acceptable salt thereof.

4g. A method for treating the symptoms of depression or anxiety associated with cocaine use disorder by a cocaine use disorder patient, in need thereof, comprising administering to said cocaine use disorder patient an effective amount of mavoglurant, or a pharmaceutically acceptable salt thereof.

5g. A method according to any one of embodiments 1g to 4g, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

6g. A method according to any one of embodiments 1g to 5g, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7g. A method according to any one of embodiments 1g to 6g, wherein administration of mavoglurant, or a pharmaceutically acceptable salt thereof is combined with standardized psychological treatment, for example, at individual or group level.

8g. A method according to any one of embodiments 1g to 7g, wherein administration of mavoglurant, or a pharmaceutically acceptable salt thereof is combined is combined with psychosocial or behavioral therapy or combination thereof, in particular contingency management based therapy.

9g. A method according to embodiment 8g, wherein the psychosocial or the behavioral therapy is computer-assisted.

10g. A method according to any one of embodiments 1g to 9g, wherein administration of mavoglurant, or a pharmaceutically acceptable salt thereof, is concomitant with methadone or buprenorphine treatment.

11g. A method according to any one of embodiments 1g to 10g, wherein mavoglurant, or a pharmaceutically acceptable salt thereof, is administered in combination with a further active agent.

12g. A method according to embodiment 11 g, wherein the further active agent is selected from a GABA agent (such as topiramate, baclofen or tiagabine) or a dopamine agent (such as bupropion, the combination of L-dopa and carbidopa).

13g. A method according to any one of embodiments 1g to 12g, wherein the patient has a genetic variation associated with a substance use disorder, such as a genetic variation associated with cocaine use disorder.

14g. A method according to any one of embodiments 1g to 13g, wherein mavoglurant, or a pharmaceutically acceptable salt thereof, is administered in an immediate-release form or a modified-release form.

15g. A method according to any one of embodiments 1g to 14g, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16g. A method according to embodiment 15g, wherein mavoglurant, or a pharmaceutically acceptable salt thereof, is administered with food.

17g. A method according to embodiment 15g or 16g, wherein mavoglurant, or a pharmaceutically acceptable salt thereof, is administered in the morning and in the evening separated by a 12 hour interval.

18g. A method according to any of the preceding embodiments, wherein cocaine use disorder is associated with binge drinking.

Embodiments (h)

1h. A method for the reduction of cocaine use by a cocaine use disorder patient, in need thereof, comprising administering to said cocaine use disorder patient a pharmaceutical composition comprising an effective amount of mavoglurant, or a pharmaceutically acceptable salt thereof, and at least one pharmaceutically acceptable excipient.

2h. A method for preventing relapse into cocaine use by a cocaine use disorder patient, in need thereof, comprising administering to said cocaine use disorder patient a pharmaceutical composition comprising an effective amount of mavoglurant, or a pharmaceutically acceptable salt thereof, and at least one pharmaceutically acceptable excipient.

3h. A method for the promotion of cocaine abstinence by a cocaine use disorder patient, in need thereof, comprising administering to said cocaine use disorder patient a pharmaceutical composition comprising an effective amount of mavoglurant, or a pharmaceutically acceptable salt thereof, and at least one pharmaceutically acceptable excipient.

4h. A method for treating the symptoms of depression or anxiety associated with cocaine use disorder by a cocaine use disorder patient, in need thereof, comprising administering to said cocaine use disorder patient a pharmaceutical composition comprising an effective amount of mavoglurant, or a pharmaceutically acceptable salt thereof, and at least one pharmaceutically acceptable excipient.

5h. A method according to any one of embodiments 1h to 4h, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

6h. A method according to any one of embodiments 1h to 5h, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7h. A method according to any one of embodiments 1h to 6h, wherein administration of the pharmaceutical composition comprising an effective amount of mavoglurant, or a pharmaceutically acceptable salt thereof, and at least one pharmaceutically acceptable excipient, is combined with standardized psychological treatment, for example, at individual or group level.

8h. A method according to any one of embodiments 1h to 7h, wherein administration of the pharmaceutical composition comprising an effective amount of mavoglurant, or a pharmaceutically acceptable salt thereof, and at least one pharmaceutically acceptable excipient, is combined with psychosocial or behavioral therapy or combination thereof, in particular contingency management based therapy.

9h. A method according to embodiment 8h, wherein the psychosocial or the behavioral therapy is computer-assisted.

10h. A method according to any one of embodiments 1h to 9h, wherein administration of the pharmaceutical composition comprising an effective amount of mavoglurant, or a pharmaceutically acceptable salt thereof, and at least one pharmaceutically acceptable excipient, is concomitant with methadone or buprenorphine treatment.

11h. A method according to any one of embodiments 1h to 10h, wherein mavoglurant, or a pharmaceutically acceptable salt thereof, is administered in combination with a further active agent.

12h. A method according to embodiment 11h, wherein the further active agent is selected from a GABA agent (such as topiramate, baclofen or tiagabine) or a dopamine agent (such as bupropion, the combination of L-dopa and carbidopa).

13h. A method according to any one of embodiments 1h to 12h, wherein the patient has a genetic variation associated with a substance use disorder, such as a genetic variation associated with cocaine use disorder.

14h. A method according to any one of embodiments 1h to 13h, wherein the pharmaceutical composition comprising mavoglurant, or a pharmaceutically acceptable salt thereof, and at least one pharmaceutically acceptable excipient, is an immediate-release form or a modified-release form.

15h. A method according to any one of embodiments 1h to 14h, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

16h. A method according to embodiment 15h, wherein the pharmaceutical composition comprising an effective amount of mavoglurant, or a pharmaceutically acceptable salt thereof, and at least one pharmaceutically acceptable excipient, is administered with food.

17h. A method according to embodiment 15h or 16h, wherein the pharmaceutical composition comprising an effective amount of mavoglurant, or a pharmaceutically acceptable salt thereof, and at least one pharmaceutically acceptable excipient, is administered in the morning and in the evening separated by a 12 hour interval.

18h. A method according to any of the preceding embodiments, wherein cocaine use disorder is associated with binge drinking.

Embodiments (i)

1j. A method for the reduction of cocaine use by a cocaine use disorder patient, in need thereof, comprising administering to said cocaine use disorder patient a pharmaceutical combination comprising an effective amount of mavoglurant, or a pharmaceutically acceptable salt thereof, and at least one further pharmaceutical active ingredient.

2j. A method for preventing relapse into cocaine use by a cocaine use disorder patient, in need thereof, comprising administering to said cocaine use disorder patient a pharmaceutical combination comprising an effective amount of mavoglurant, or a pharmaceutically acceptable salt thereof, and at least one at least one further pharmaceutical active ingredient.

3j. A method for the promotion of cocaine abstinence by a cocaine use disorder patient, in need thereof, comprising administering to said cocaine use disorder patient a pharmaceutical combination comprising an effective amount of mavoglurant, or a pharmaceutically acceptable salt thereof, and at least one at least one further pharmaceutical active ingredient.

4j. A method for treating the symptoms of depression or anxiety associated with cocaine use disorder by a cocaine use disorder patient, in need thereof, comprising administering to said cocaine use disorder patient a pharmaceutical combination comprising an effective amount of mavoglurant, or a pharmaceutically acceptable salt thereof, and at least one at least one further pharmaceutical active ingredient.

5j. A method according to any one of embodiments 1j to 4j, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

6j. A method according to any one of embodiments 1j to 5j, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

7j. A method according to any one of embodiments 1j to 6j, wherein administration of the pharmaceutical combination comprising an effective amount of mavoglurant, or a pharmaceutically acceptable salt thereof, and at least one further pharmaceutical active ingredient, is combined with standardized psychological treatment, for example, at individual or group level.

8j. A method according to any one of embodiments 1j to 7j, wherein administration of the pharmaceutical combination comprising an effective amount of mavoglurant, or a pharmaceutically acceptable salt thereof, and at least one further pharmaceutical active ingredient, is combined with psychosocial or behavioral therapy or combination thereof, in particular contingency management based therapy.

9j. A method according to embodiment 8j, wherein the psychosocial or the behavioral therapy is computer-assisted.

10j. A method according to any one of embodiments 1j to 9j, wherein administration of the pharmaceutical combination comprising an effective amount of mavoglurant, or a pharmaceutically acceptable salt thereof, and at least one further pharmaceutical active ingredient, is concomitant with methadone or buprenorphine treatment.

11j. A method according to embodiment 10j, wherein the further active agent is selected from a GABA agent (such as topiramate, baclofen or tiagabine) or a dopamine agent (such as bupropion, the combination of L-dopa and carbidopa).

12j. A method according to any one of embodiments 1j to 11j, wherein the patient has a genetic variation associated with a substance use disorder, such as a genetic variation associated with cocaine use disorder.

13j. A method according to any one of embodiments 1j to 12j, wherein the pharmaceutical combination comprising mavoglurant, or a pharmaceutically acceptable salt thereof, and at least one further pharmaceutical active ingredient, is an immediate-release form or a modified-release form.

14j. A method according to any one of embodiments 1j to 13j, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

15j. A method according to embodiment 14j, wherein the pharmaceutical combination comprising an effective amount of mavoglurant, or a pharmaceutically acceptable salt thereof, and at least one further pharmaceutical active ingredient, is administered with food.

16j. A method according to embodiment 14j or 15j, wherein the pharmaceutical combination comprising an effective amount of mavoglurant, or a pharmaceutically acceptable salt thereof, and at least one further pharmaceutical active ingredient, is administered in the morning and in the evening separated by a 12 hour interval.

17j. A method according to any of the preceding embodiments, wherein cocaine use disorder is associated with binge drinking.

Further Embodiments

Embodiment 1: Mavoglurant, or a pharmaceutically acceptable salt thereof, for use in the reduction of cocaine use by a cocaine use disorder patient.

Embodiment 2: Mavoglurant, or a pharmaceutically acceptable salt thereof, for use in preventing relapse into cocaine use by a cocaine use disorder patient.

Embodiment 3: Mavoglurant, or a pharmaceutically acceptable salt thereof, for use in the promotion of cocaine abstinence by a cocaine use disorder patient.

Embodiment 4: Mavoglurant, or a pharmaceutically acceptable salt thereof, for use in the treatment of the symptoms of depression or anxiety associated with cocaine use disorder.

Embodiment 5: Mavoglurant, or a pharmaceutically acceptable salt thereof, for use according to any one of embodiments 1 to 4, wherein cocaine use disorder is associated with cocaine inhalation (i.e. smoking), intravenous cocaine, cocaine nasal insufflation (i.e. snorting) or oral formulations of cocaine; in particular is associated with cocaine inhalation (i.e. smoking).

Embodiment 6: Mavoglurant, or a pharmaceutically acceptable salt thereof, for use according to any one of embodiments 1 to 5, wherein cocaine use disorder is comorbid with a psychiatric disorder, such as antisocial personality disorder, borderline personality disorder, depression, anxiety, schizophrenia, attention deficit hyperactivity disorder, bipolar disorder, obsessive compulsive disorder or binge eating disorder.

Embodiment 7: Mavoglurant, or a pharmaceutically acceptable salt thereof, for use according to any one of embodiments 1 to 6, wherein the use is combined with standardized psychological treatment, for example, at individual or group level.

Embodiment 8: Mavoglurant, or a pharmaceutically acceptable salt thereof, for use according to any one of embodiments 1 to 7, wherein the use is combined with psychosocial or behavioral therapy or combination thereof, in particular contingency management based therapy.

Embodiment 9: Mavoglurant, or a pharmaceutically acceptable salt thereof, for use according to embodiment 8, wherein the psychosocial or the behavioral therapy is computer-assisted.

Embodiment 10: Mavoglurant, or a pharmaceutically acceptable salt thereof, for use according to any one of embodiments 1 to 9, wherein the use is concomitant with methadone or buprenorphine treatment.

Embodiment 11: Mavoglurant, or a pharmaceutically acceptable salt thereof, for use according to any one of embodiments 1 to 10, wherein mavoglurant, or a pharmaceutically acceptable salt thereof, is administered in combination with a further active agent.

Embodiment 12: Mavoglurant, or a pharmaceutically acceptable salt thereof, for use according to any one of embodiments 1 to 11, wherein the patient has a genetic variation associated with a substance use disorder, such as a genetic variation associated with cocaine use disorder.

Embodiment 13. Mavoglurant, or a pharmaceutically acceptable salt thereof, for use according to any one of embodiments 1 to 12, wherein mavoglurant, or a pharmaceutically acceptable salt thereof, is administered in an immediate-release form or a modified-release form.

Embodiment 14: Mavoglurant, or a pharmaceutically acceptable salt thereof, for use according to any one of embodiments 1 to 13, wherein mavoglurant, or a pharmaceutically acceptable salt thereof, is administered in an amount of from 50 mg/b.i.d to 200 mg/b.i.d, in particular 50 mg/b.i.d., 100 mg/b.i.d or 200 mg/b.i.d., such as 200 mg/b.i.d.

Embodiment 15: Mavoglurant, or a pharmaceutically acceptable salt thereof, for use according to any of the preceding embodiments, wherein cocaine use disorder is associated with binge drinking.

Embodiment 16: A combination comprising mavoglurant, or a pharmaceutically acceptable salt thereof, and at least one further active agent selected from the group consisting of a GABA agent (e.g. topiramate, tiagabine, baclofen or vigabatrin), an agonist replacement agent (e.g. modafinil, methylphenidate, methadone or buprenorphine), a dopamine agent (e.g. bupropion, the combination of levodopa with carbidopa, risperidone, olanzapine, aripiprazole or dextroamphetamine), a D3 receptor ligand (e.g. CJB090), a corticotropin-releasing factor (CRF) receptor antagonist (e.g. CP154,526), a cannabinoid CB1 receptor antagonist, a dual dopamine-serotonin releaser (e.g. PAL-287), a noradregenic agent (e.g. doxazosin, disulfiram or nepicastat), a 5-$HT_{1A}$ receptor partial agonist (e.g. buspirone), a MU opiod agonist (e.g. buprenorophine), a NET inhibitor (e.g. desipramine) and a NMDA receptor antagonist (e.g. amantadine); or pharmaceutically acceptable salts thereof.

General Terms

The term "cocaine use disorder" or "CUD", as used herein, is defined with reference to DSM-5 criteria (i.e. according to the Diagnostic and Statistical Manual of Mental Disorders. 5$^{th}$ Edition, Washington, D.C.: American Psychiatric Association, 2013), the entire contents of which are incorporated herein by reference. As used herein, the term "cocaine use disorder" is defined as a problematic pattern of cocaine use leading to clinically significant impairment or distress, as manifested by at least two of the following, occurring within a 12-month period:
1) Cocaine is often taken in larger amounts or over a longer period than was intended.
2) There is a persistent desire or unsuccessful efforts to cut down or control cocaine use.
3) A great deal of time is spent in activities necessary to obtain cocaine, use cocaine, or recover from its effects.
4) Craving, or a strong desire or urge to use cocaine.
5) Recurrent cocaine use resulting in a failure to fulfill major role obligations at work, school, or home.
6) Continued cocaine use despite having persistent or recurrent social or interpersonal problems caused or exacerbated by the effects of cocaine.
7) Important social, occupational, or recreational activities are given up or reduced because of cocaine use.
8) Recurrent cocaine use in situations in which it is physically hazardous.
9) Cocaine use is continued despite knowledge of having a persistent or recurrent physical or psychological problem that is likely to have been caused or exacerbated by cocaine.
10) Tolerance, as defined by either of the following: a) A need for markedly increased amounts of cocaine to achieve intoxication or desired effect; b) A markedly diminished effect with continued use of the same amount of cocaine.
11) Withdrawal, as manifested by either of the following:
   a) The characteristic withdrawal syndrome for cocaine:
      i) cessation of (or reduction in) prolonged cocaine use;
      ii) dysphoric mood and two (or more) of the following physiological changes, developing within a few hours to several days after the cessation of (or reduction in) cocaine use: fatigue; vivid, unpleasant dreams; insomnia or hypersomnia; increased appetite; psychomotor retardation or agitation.
   b) Cocaine is taken to relieve or avoid withdrawal symptoms.

"Cocaine use disorder" may be separated into the following three categories: mild (i.e. presence of 2 to 3 symptoms, defined with reference to DSM-5 criteria), moderate (i.e. presence of 4 to 5 symptoms, defined with reference to DSM-5 criteria) and severe (i.e. presence of 6 or more symptoms, defined with reference to DSM-5 criteria). In one embodiment "cocaine use disorder", as used herein, refers to "mild cocaine use disorder", "moderate cocaine use disorder" and "severe cocaine use disorder". In a further embodiment, "cocaine use disorder", as used herein, refers to "mild cocaine use disorder", "moderate cocaine use disorder" or "severe cocaine use disorder".

The term "cocaine use disorder patient" refers to a patient diagnosed with CUD, as defined herein. In one embodiment, the term "cocaine use disorder patient" refers to a patient diagnosed with CUD who is in abstinence from cocaine, for example, for at least 1 day, such as 3 days or more. The term "cocaine use disorder patient in abstinence from cocaine" refers to a patient diagnosed with CUD in abstinence from cocaine for a period, for example, for at least 1 day. The term "cocaine use disorder associated with binge drinking" refers to a patient that is diagnosed with cocaine use disorder and is an abuser of alcohol (i.e. a heavy drinker). Abusers of alcohol may not drink on a consistent basis, for example, they may only drink once a week, but, when drinking, they may drink heavily, which will cause problems, such as suffering from alcohol intoxication. For the sake of clarity, herein, an abuser of alcohol is not an alcohol use disorder patient (i.e. does not meet criteria for alcohol use disorder as defined with reference to DSM-5 criteria). The term "heavy drinker" refers to someone with a heavy alcohol use pattern. According to the National Institute on Alcohol Abuse and Alcoholism (NIAAA), the Substance Abuse and Mental Health Services Administration (SAMHSA) defines "heavy alcohol use" as binge drinking on 5 or more days in the past month. NIAAA defines binge drinking as a pattern of drinking that brings blood alcohol concentration (BAC) levels to 0.08 g/dl. This typically occurs after 4 alcoholic drinks for women and 5 alcoholic drinks for men—in about 2 hours. The Substance Abuse and Mental Health Services Administration (SAMHSA), defines "binge drinking" as 5 or more alcoholic drinks for males or 4 or more alcoholic drinks for females on the same occasion (i.e., at the same time or within a couple of hours of each other) on at least 1 day in the past month. The term "alcohol", as used herein, for example in relation to "drinks", "alcoholic drinks" or "drinking", refers to ethyl alcohol (i.e. ethanol). The term "drinking", "drinks" or "alcoholic drinks", as used herein, is understood in the context of "standard drinks", such as spirits or blends that are intended for human consumption, wherein a "standard drink" equals 12 g ethanol.

The term "cocaine", as used herein, refers to cocaine itself (the free base benzoylmethylecgonine), a salt thereof, such as cocaine hydrochloride, or cocaine preparations, such as coca leaves, coca paste, and cocaine alkaloids (such as crack), wherein, in all forms of the substance, cocaine is the active ingredient. The term "cocaine craving" as used herein refers to a conscious desire or urge to consume cocaine.

The term "cocaine use", as used herein, refers to cocaine consumption.

The term "reducing cocaine use" or "reduction of cocaine use", as used herein, refers to reducing the amount or frequency of cocaine use, for example as assessed by urinalysis (e.g. by measuring metabolites of cocaine in urine, such as benzoylecgonine) or as assessed by using self-reported cocaine use with standardized tools like the Timeline Follow-Back self-report (Sobell L C, Sobell M B, 1996, Timeline FollowBack user's guide: A calendar method for assessing alcohol and drug use. Addiction Research Foundation, Toronto, Ontario, Canada; *J. Anal. Toxicolo.*, 2002, 26: 393-400).

The term "cocaine abstinence" or "in abstinence from cocaine", as used herein, refers to not taking cocaine. The term "promoting cocaine abstinence" or "promotion of cocaine abstinence", as used herein, refers to help maintaining abstinence from cocaine use, in particular after at least 1 day of not taking cocaine, for example maintaining abstinence from cocaine use for a period of, for example, at least 1 week, 2 weeks, 3 weeks, 1 month, 3 months, 6 months or more, in particular at least 1 week or more, such as 2 weeks.

The term "relapse into cocaine use" or "relapse into cocaine consumption", as used herein, refers to a cocaine intake (i.e. taking cocaine) following a period of cocaine abstinence, for example following a period of cocaine abstinence of at least 1 day or more, such as 3 days, 1 week, 2 weeks, 3 weeks, 1 month, 3 months, 6 months or more.

The term "preventing relapse into cocaine use" or "preventing relapse into cocaine consumption", as used herein, refers to the prevention of cocaine intake by a CUD patient after the patient has stopped the intake of cocaine, in particular after 1 day or more of not taking cocaine. In some embodiments, the term encompasses the permanent stoppage of cocaine intake. In other embodiments, the term encompasses a delay in the resumption of cocaine intake as compared to the time to resumption by a subject that is not administered a compound of the invention. The delay in resumption can be, e.g., days (e.g., 2, 3, 4, 5, 6, 7 days), weeks (e.g., 1, 2, 3 weeks), months (e.g., 1, 2, 3, 4, 5, 6 months), or longer.

The term "psychosocial or behavioral therapy", as used herein, refers to, but not limited to, cognitive behavioral therapy (e.g. as described in Arch. Gen. Psychiatry 1999; 56:493-502), interpersonal therapy (e.g. as described in *Psychol Addict Behav* 2009; 23(1): 168-174), contingency management based therapy (e.g. as described in *Psychol Addict Behav* 2009; 23(1): 168-174; in *J. Consul. Clin. Psychol.* 2005; 73(2): 354-59; or in *Case Reports in Psychiatry*, Vol. 2012, Article ID 731638), community reinforcement approach based therapy (e.g. as described in *Drug Alcohol Depend* 2004; 74:1-13), motivational interviewing based therapy (e.g. as described in *J. Consul. Clin. Psychol.* 2001; 69(5): 858-62), motivational enhancement based therapy (e.g. as described in *Drug Alcohol Depend* 2007; 91:97-101) or meditation based therapy, such as transcendental meditation based therapy (e.g. as described in Addiction 2004; 99(7):862-874 or *J. Consul. Clin. Psychol.* 2000; 68(3): 515-52); in particular contingency management based therapy.

The term "standardized psychological treatment" or ""standardized psychological support", as used herein, refers to standard counselling sessions, for example once a week, in particular counselling focused on cocaine consumption.

The term "computer-assisted" in the expression "the psychosocial or the behavioral therapy is computer-assisted", as used herein, refers to psychosocial or behavioral therapy comprising the use of electronic tools such as online tools, smartphones, wireless devices or health Apps. In one embodiment, the term "computer-assisted" in the expression "the psychosocial or the behavioral therapy is computer-assisted", as used herein, is to be understood as "computer-implemented" (i.e. the psychosocial or the behavioral therapy is computer-implemented).

The term "administered with food" refers to, for example, any food product, solid or liquid, with caloric content. The dosage of the mavoglurant, or pharmaceutically acceptable salt thereof, may be administered to a subject, for example, between thirty minutes prior to eating food, to, for example, one hour after consumption. In particular, administration of mavoglurant, or pharmaceutically acceptable salt thereof, occurs immediately after consuming food up to about thirty minutes after consumption.

The term "genetic variation" refers to a change in a gene sequence relative to a reference sequence (e.g., a commonly-found and/or wild-type sequence). Genetic variation may be recombination events or mutations such as substitution/deletion/insertion events like point and splice site mutations. In one embodiment, the genetic variation is a genetic variation in mGluR5.

The term "treat" "treating" "treatment" or "therapy", as used herein, means obtaining beneficial or desired results, for example, clinical results. Beneficial or desired results can include, but are not limited to, alleviation of one or more symptoms of cocaine use disorder patients, as defined herein, such as anxiety symptoms or depression symptoms associated with cocaine use disorder, in particular by a cocaine use disorder patient in abstinence from cocaine, as herein defined. One aspect of the treatment is, for example, that said treatment should have a minimal adverse effect on the patient, e.g. the agent used should have a high level of safety, for example without producing the side effects of previously known treatment regimens. The term "alleviation", for example in reference to a symptom of a condition, as used herein, refers to reducing at least one of the frequency and amplitude of a symptom of a condition in a patient.

The term "concomitant", as used herein, for example in relation to "concomitant with methadone or buprenorphine treatment", refers to both simultaneous and sequential administration.

As used herein, the term "subject" refers to a mammalian organism, preferably a human being (male or female).

As used herein, the term "patient" refers to a subject who is diseased and would benefit from the treatment.

As used herein, a subject is "in need of" a treatment if such subject (patient) would benefit biologically, medically or in quality of life from such treatment.

The term "pharmaceutical composition" is defined herein to refer to a mixture or solution containing at least one active ingredient or therapeutic agent to be administered to a subject, in order to treat a particular condition (i.e. disease, disorder or condition or at least one of the clinical symptoms thereof) affecting the subject.

As used herein, the term "pharmaceutically acceptable excipient" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 22$^{nd}$ Ed. Mack Printing Company, 2013, pp. 1049-1070). Except insofar as any conventional carrier is incompatible with the active ingredient, its use in the therapeutic or pharmaceutical compositions is contemplated.

The terms "drug", "active substance", "active ingredient", "pharmaceutically active ingredient", "active agent" or "therapeutic agent" are to be understood as meaning a compound in free form or in the form of a pharmaceutically acceptable salt, in particular compounds of the type specified herein. In particular, reference to mavoglurant, or a pharmaceutically acceptable salt thereof, in combination with a further active agent, as used herein (e.g. in any of embodiments (a) to (j), herein above, or in any of the claims, herein below), refers to mavoglurant in combination with at least one further active agent selected from a GABA agent (e.g. topiramate, tiagabine, baclofen or vigabatrin), an agonist replacement agent (e.g. modafinil, methylphenidate, methadone or buprenorphine), a dopamine agent (e.g. bupropion, the combination of levodopa with carbidopa, risperidone, olanzapine, aripiprazole or dextroamphetamine), a D3 receptor ligand (e.g. CJB090), a corticotropin-releasing factor (CRF) receptor antagonist (e.g. CP154,526), a cannabinoid CB1 receptor antagonist, a dual dopamine-serotonin releaser (e.g. PAL-287), a noradregenic agent (e.g. doxazosin, disulfiram or nepicastat), a 5-HT$_{1A}$ receptor partial agonist (e.g. buspirone), a MU opiod agonist (e.g. buprenorophine), a NET inhibitor (e.g. desipramine) and a NMDA receptor antagonist (e.g. amantadine); or pharmaceutically acceptable salts thereof.

The term "immediate release form" refers to a pharmaceutical composition designed to release the active substance immediately upon in vivo administration.

The term "modified release form" refers to a pharmaceutical composition which releases the active substance not immediately, but offers a sustained, retard, continuous, gradual, prolonged or pulsatile release and therefore alters drug plasma levels distinctively versus an immediate release form. The term "modified release form" encompasses forms that are described as controlled-release form, sustained-release form, extended-release form, and long-acting form; in particular a sustained-release form.

The term "combination" or "pharmaceutical combination" refers to either a fixed combination in one unit dosage form (e.g., capsule, tablet, caplets or particulates), non-fixed combination, or a kit of parts for the combined administration where a compound of the present invention and one or more combination partner (e.g. another drug as specified herein, also referred to as further "pharmaceutical active ingredient", "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "fixed combination" means that the active ingredients, e.g. the compound of the present invention and one or more combination partners, are both administered to a patient simultaneously in the form of a single entity or dosage. The term "non-fixed combination" means that the active ingredients, e.g. a compound of the present invention and one or more combination partners, are both administered to a patient as separate entities either simultaneously or sequentially with no specific time limits, wherein such administration provides therapeutically effective levels of the two compounds in the body of the patient.

The compound of the present invention may be administered separately, by the same or different route of administration, or together in the same pharmaceutical composition as the other agents. In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

As used herein, the term "a," "an," "the" and similar terms used in the context of the present invention (especially in the context of the claims) are to be construed to cover both the singular and plural unless otherwise indicated herein or clearly contradicted by the context.

The use of any and all examples, or exemplary language (e.g. "such as") provided herein is intended merely to better illuminate the invention and does not pose a limitation on the scope of the invention otherwise claimed.

As used herein, the compound of the invention, alternatively named Compound (1), as used herein above and below, is the mGluR5 antagonist (−)-(3aR,4S,7aR)-4-Hydroxy-4-m-tolylethynyl-octahydro-indole-1-carboxylic acid methyl ester, also named (−)-(3aR,4S,7aR)-4-Hydroxy-4-[2-(3-methylphenyl)ethynyl]perhydroindole-1-carboxylic acid methyl ester, also known as mavoglurant, of formula:

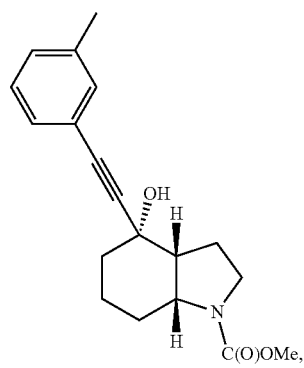

which can be e.g. prepared as described in WO2003/047581, e.g., in Example 1, or as described in WO2010/018154. WO2003/047581, which is incorporated herein by reference, also describes its in-vitro biological data, as per page 7. As used herein, "mavoglurant" refers to the free form, and any reference to "a pharmaceutically acceptable salt thereof" refers to a pharmaceutically acceptable acid addition salt thereof. As used herein, the term "mavoglurant, or a salt thereof, such as a pharmaceutically acceptable salt thereof", as used in the context of the present invention (especially in the context of the any of the embodiments, above or below, and the claims) is thus to be construed to cover both the free form and a pharmaceutically acceptable salt thereof, unless otherwise indicated herein.

In one embodiment, Compound (I) is also intended to represent isotopically labeled forms. Isotopically labeled compounds have structures depicted by the formula above except that one or more atoms are replaced by an atom having a selected atomic mass or mass number. Isotopes that can be incorporated into the compound of the invention include, for example, isotopes of hydrogen, namely the compound of formula:

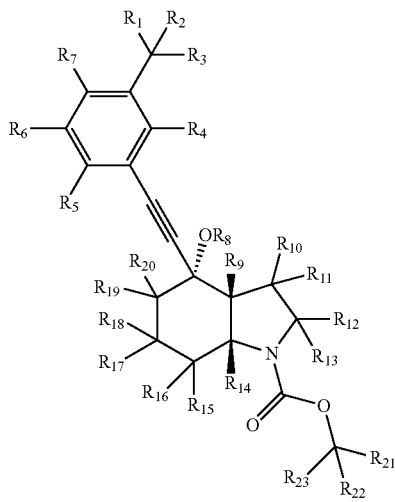

wherein each $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$ and $R_{23}$ is independently selected from H or deuterium; provided that there is at least one deuterium present in the compound. In other embodiments there are multiple deuterium atoms present in the compound.

Further, incorporation of certain isotopes, particularly deuterium (i.e., $^2H$ or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of the compound of the invention. The concentration of deuterium, may be defined by the isotopic enrichment factor. The term "isotopic enrichment factor" as used herein means the ratio between the isotopic abundance and the natural abundance of a specified isotope. If a substituent in the compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into the compound of the invention include isotopes of hydrogen, other than deuterium, carbon, nitrogen, oxygen, and fluorine such as $^3H$, $^{11}C$, $^{13}C$, $^{14}C$, $^{15}N$, $^{18}F$ respectively. Accordingly it should be understood that the invention includes compounds that incorporate one or more of any of the aforementioned isotopes, including for example, radioactive isotopes, such as $^3H$ and $^{14}C$, or those into which non-radioactive isotopes, such as $^2H$ and $^{13}C$ are present. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. The isotopically-labeled compounds can generally be prepared by conventional techniques known to those skilled in the art or by processes analogous to those described preparation of the compound of the invention by using an appropriate isotopically-labeled reagents in place of the non-labeled reagent previously employed.

As used herein, the terms "free form" or "free forms" refers to the compound in non-salt form, such as the base free form or the acid free form of a respective compound, e.g. the compounds specified herein (e.g. mavoglurant or further pharmaceutical active ingredient, for example, as defined herein).

As used herein, the terms "salt", "salts" or "salt form" refers to an acid addition or base addition salt of a respective compound, e.g. the compounds specified herein (e.g. mavoglurant or further pharmaceutical active ingredient, for example, as defined herein). "Salts" include in particular "pharmaceutically acceptable salts". The term "pharmaceutically acceptable salts" refers to salts that retain the biological effectiveness and properties of the compounds and, which typically are not biologically or otherwise undesirable. The compounds, as specified herein (e.g. mavoglurant or further pharmaceutical active ingredient, for example, as defined herein), may be capable of forming acid and/or base salts by virtue of the presence of amino and/or carboxyl groups or groups similar thereto. The compound of the invention is capable of forming acid addition salts, thus, as used herein, the term pharmaceutically acceptable salt of mavoglurant means a pharmaceutically acceptable acid addition salt of mavoglurant.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

Pharmaceutically acceptable salts can be synthesized from a basic or acidic moiety, by conventional chemical methods. Generally, such salts can be prepared by reacting the free acid forms of the compound with a stoichiometric amount of the appropriate base (such as Na, Ca, Mg, or K hydroxide, carbonate, bicarbonate or the like), or by reacting the free base form of the compound with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", $22^{nd}$ edition, Mack Publishing Company (2013); and in "Handbook of Pharmaceutical Salts: Properties, Selection, and Use" by Stahl and Wermuth (Wiley-VCH, Weinheim, 2011, $2^{nd}$ edition).

The compounds specified herein (e.g. mavoglurant or the further pharmaceutical active ingredient, for example, as defined herein) can be administered by conventional route, in particular orally, such as in the form of tablets, capsules, caplets or particulates, which can be manufactured according to pharmaceutical techniques as known in the art (for example in "Remington Essentials of Pharmaceutics, 2013, $1^{st}$ Edition, edited by Linda Felton, published by Pharmaceutical Press 2012, ISBN 978 0 85711 105 0; in particular Chapter 30), wherein pharmaceutical excipients are, for example, as described in "Handbook of Pharmaceutical Excipients, 2012, $7^{th}$ Edition, edited by Raymond C. Rowe, Paul J. Sheskey, Walter G. Cook and Marian E. Fenton, ISBN 978 0 85711 027 5". In particular, WO2014/199316 describes formulations comprising mavoglurant, in particular modified release formulations thereof, and is incorporated herein by reference, more particularly the Examples, the preferred embodiments and claims therein.

The pharmaceutical composition or combination of the present invention can be in a unit dosage form (e.g. tablet, capsule, caplet or particulate) comprising an amount ranging of from 1 mg to 300 mg, in particular of from 50 mg to 200 mg, such as 50 mg to 100 mg, more particularly 200 mg, of mavoglurant (referring to an amount of the free form of mavoglurant, and if a salt thereof is used the amount will be adapted accordingly; in particular mavoglurant is in the free form). For the above-mentioned uses/treatment methods the appropriate dosage may vary depending upon a variety of factors, such as, for example, the age, weight, sex, the route of administration or salt employed. In patients with, for example, of from 50-70 kg body weight, an indicated daily dosage is, for example, 200 mg/b.i.d (referring to an amount of the free form of mavoglurant, and if a salt thereof is used the amount will be adapted accordingly).

Abbreviations

BE=Benzoylecgonine
EtG=Ethyl Glucuronide
CM=Contingency Management
DSM 5=Diagnostic and Statistical Manual of Mental Disorders, 5th Ed.
CUD=Cocaine Use Disorder
PK=Pharmacokinetic
TLFB=Timeline Follow-Back
mg=milligram
bid=b.i.d=twice (two times) a day
mmHg=millimiter of mercury
msec=millisecond
HIV=human immunodeficiency virus
ELISA=enzyme-linked immunosorbent assay
ECG=electrocardiogram
QT=time between the start of the Q wave and the end of the T wave
T wave=positive deflection after each QRS complex
ST wave=time between the start of the S wave and the end of the T wave
QRS=time between the start of the Q wave and the end of the T wave
QTcF=Fridericia QT correction formula
SoA=standard of care
SSRI=Selective serotonin reuptake inhibitors
C-SSRS=Columbia Suicide Severity Rating Scale
hCG=human chorionic gonadotropin
AST=aspartate aminotransferase
ALT=alanine aminotransferase
ULN=upper limit of normal
GGT=gamma-glutamyl transpeptidase
AV block=Atrioventricular block
UDS=urinary drug screening
MDMA=3,4-methylenedioxy-methamphetamine
MDEA=3,4-methylenedioxy-N-ethylamphetamine
MDA=3,4-methylenedioxy-amphetamine

EXAMPLES

The following Examples serve to illustrate the invention without limiting the scope thereof. The term "mavoglurant", as used in the context of these examples, refers to the free form.

Example 1

Evaluation of the Effects of Mavoglurant on Cocaine Dependence and Cocaine Reinstatement Using the Intravenous Self-Administration Model in Sprague-Dawley Rats Animals Adult male Sprague-Dawley rats (300-325 g at arrival) from Harlan Laboratory (Indiana, USA) were used. Upon arrival, the rats were assigned a unique identification numbers (tail marks). Animals were single housed in suspended polycarbonate rat cages with filter tops, and were acclimated for up to 7 days. All rats were examined, handled, and weighed prior to initiation of the study to assure adequate health and suitability. During the course of the study, 12 h/12 h light/dark cycles were maintained. The room temperature was 21-23° C. with a relative humidity maintained at 30-70%. Water was provided ad libitum for the duration of the study.

Test Compounds

Cocaine Hydrochloride (Sigma-Aldrich, USA) (1.05 mg/ml which is equivalent to 0.3 mg/kg/infusion under 350 g body weight and 0.1 ml/infusion rate) was dissolved in saline (0.9% NaCl). The formulation was a clear solution.

Mavoglurant (free form) was formulated in 0.5% methylcellulose (MC) at 1, 3 and 10 mg/kg and administered orally at a dose volume of 1 ml/kg 60 minutes prior to test.

Apparatus

Intravenous drug self-administration took place in sound attenuated operant chambers equipped with an exhaust fan (Med Associates, VT). Each chamber contained two levers situated on one wall of the chamber. Only one of the two levers was active (located on the left side). Pressing the active lever caused delivery of reinforcer (food or cocaine). The other lever was "inactive", i.e. pressing it did not deliver any reinforcement. A stimulus light was located above each lever, but only the one above the active lever was on during the timeout period (defined below). A house light (providing illumination) was located at the top of opposite wall. For food training (see details below), a pellet receptacle was situated between the two levers for delivery of food pellets (Bio-Serv's Dustless Precision Pellets #F0165, 45 mg). An infusion pump mounted above each chamber delivered drug solution via Tygon tubing connected to a single channel fluid swivel, which was mounted on a balance arm above the operant chamber. The output of the liquid swivel was attached to the externalized terminus of the intravenous catheter.

Methods

Phase I: Acute Effects of Mavoglurant on Cocaine Self-Administration in Rats

Food Training and Surgery

Prior to intravenous catheterization surgery, rats were trained to press the active lever to obtain food. Food training started after the rats were food-restricted and reached approximately 85% of the free-feeding body weight. After acquiring the lever-press response to obtain food, rats were implanted with a jugular vein catheter (Access Technologies, USA). Catheters were flushed daily with a 0.2 ml Heparin-Enrofloxacin solution to avoid clogging and to ensure smooth drug infusion. The flushing liquid was made in 50 ml volume unit which contained 1500U Heparin and 320 mg Enrofloxacin (Baytril®). The solution was stored in sterilized vials in 4° C. refrigerator. The rats were on free feeding two days prior to surgery and throughout recovery.

During the study, Methohexital sodium (Brevital®, Henry Schein Animal Health, USA) was used to confirm proper infusion via the implanted catheter. Brevital is a short-acting barbiturate that, when infused through the catheter, produces overt signs of sedation within seconds. The Brevital test (0.2 ml of 1% solution) was performed after acquisition sessions of both Phases and after compound test session of Phase I. Animals that showed no immediate signs of sedation were removed from the experiment.

Acquisition of the Cocaine Self-Administration Response

One week after the surgery, single housed rats were food restricted and maintained at ~85% of their free-feeding age-matched control body weight throughout the study. Rats were then allowed to self-administer cocaine by pressing the active lever on a fixed-ratio (FR) schedule of reinforcement. In this study a FR5 schedule was used, i.e. five lever presses for one cocaine delivery. The dose of cocaine was 0.3 mg/kg/infusion, which equals to 0.105 mg per rat (350 g) in each infusion (0.1 ml solution). Each cocaine infusion lasted 1.0 sec. Delivery of cocaine was followed by a 20 second timeout period, during which no drug was delivered even if the active lever was pressed. During timeout, the stimulus light above the active lever was on. After 15 days of training, all rats demonstrated a high and stable number of lever presses for cocaine. Each training or testing session lasted 1 hour.

Pharmacological Treatment with Mavoglurant

Pharmacological studies were initiated after a stable cocaine self-administration baseline was established (less than 20% variation in daily amount of drug infusions over 3 consecutive days; a minimum of 6 drug infusions per session). Pharmacological studies were conducted twice a week (usually on Wednesday and Friday), and baseline cocaine training were maintained on other days.

N=12

Vehicle

Mavoglurant 1 mg/kg

Mavoglurant 3 mg/kg

Mavoglurant 10 mg/kg

Phase II: Effects of Mavoglurant on Cue-Induced Reinstatement of the Self-Administration Response Food Training and Surgery The methods for food training, catheter surgery, flushing and infusion confirmation were the same as those in Phase I.

Acquisition

Cocaine self-administration training in this stage was conducted in a separate cohort of rats (N=32). The methods of training were the same as those in Phase I, but the cues (light flash plus tone) appeared concurrently during cocaine infusion, and the cue light stayed on during the 20 second timeout period. As in Phase I, rats underwent 15 days of acquisition training.

Extinction and Cue-Induced Reinstatement

After a stable rate of cocaine self-administration was achieved, the rats underwent a 9-day extinction procedure, which was similar to acquisition training except that pressing the active lever led to saline infusion instead of cocaine. During extinction sessions no cues were presented after an active lever-press. Rats were all reached the criterion for extinction (number of infusions≤5, i.e. number of active lever responses <30 in the 1-hour session) in day 9 (last day) of extinction training.

During the reinstatement session, which occurred one day after the last extinction session, rats were presented the cues (flash+tone) at the beginning of the session and their lever-press responses recorded. There was no cocaine infusion during this reinstatement session, subject only received saline on a FR5 schedule. An independent groups design was used for this study, i.e. ~ half of rats (N=15 after infusion confirmation) were administered with an optimal dose of mavoglurant and ~ half (N=14 after infusion confirmation) with vehicle before the reinstatement session. Based on the results of Phase I, the optimal dose of mavoglurant used in Phase II was 10 mg/kg.

Results

Phase I: Acute Effects of Mavoglurant on Cocaine Self-Administration

Acquisition of Cocaine Dependence

The acquisition of the cocaine self-administration response in Phase I is illustrated in FIG. 1. Twelve rats per group were included in this study after confirmation of proper infusion with Brevital. Cocaine self-administration increased steadily during the first week of training and stabilized during the second week of training. Learning was confirmed by a two-way ANOVA (Training day effect: $F[14,330]=6.199$; $P<0.001$). There was also a significant group x day interaction ($F[1,330]=4.850$, $P<0.05$), however post hoc comparisons did not indicate any significant differences between groups on each training day, thus confirming comparable self-administration performance between groups (sub-cohorts).

Acute Effects Mavoglurant on Cocaine Self-Administration

For sub-cohort I-b, a one-way ANOVA with repeated measures confirmed a significant effect of mavoglurant [Treatment effect: $F(3,33)=6.358$; $P<0.01$]. Post hoc comparisons further confirmed that mavoglurant tended to reduce responding on the active lever at 3 mg/kg ($p<0.10$) and significantly reduced responding at 10 mg/kg ($p<0.001$).

Figure 3:
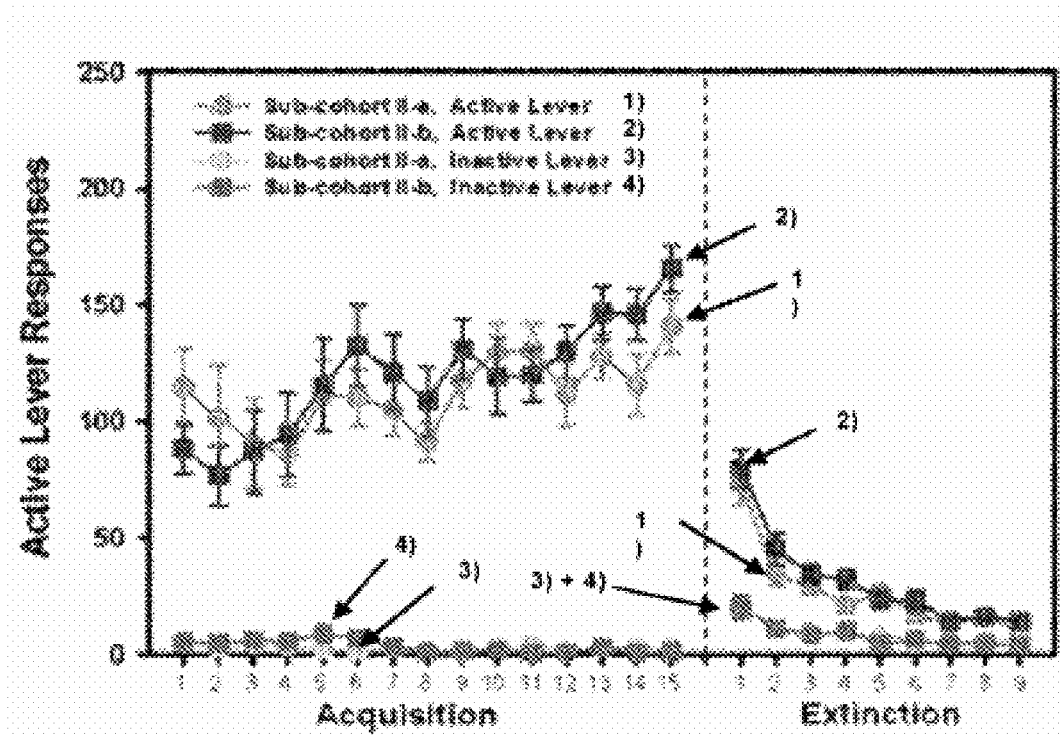
FIG. 3: Acquisition and extinction of the cocaine self-administration response in two sub-cohorts of rats (Phase II). Data represent the means+SEM. N=14-15 per group.

Phase II: Effects of Mavoglurant on Cue-Induced Reinstatement of Self-Administration Acquisition and Extinction of Cocaine Dependence Acquisition of the cocaine self-administration response is illustrated in FIG. 3. The two groups (sub-cohorts) included 14 and 15 rats after confirmation of proper infusion with Brevital. Like in Phase 1, cocaine self-administration increased steadily during the first week of training and stabilized during the second week of training. A two-way ANOVA confirmed a significant effect of training day ($F[14, 405]=3.463$; $P<0.001$) and no differences between sub-cohorts ($F[1,405]=1.538$, n.s.), indicating comparable learning performance between groups.

During the extinction phase there was a progressive and significant reduction of responses on the active lever, which was confirmed by a two-way ANOVA (Day effect: $F[8,243]=41.635$; $P<0.001$). There was also a significant main effects of sub-cohorts ($F[1,243]=5.306$, $P<0.05$), however post hoc comparisons indicated comparable performance between groups during each extinction session. All rats reached the criteria for extinction by 9 days of training.

Cue-Induced Reinstatement of the Self-Administration Response

Figure 4:
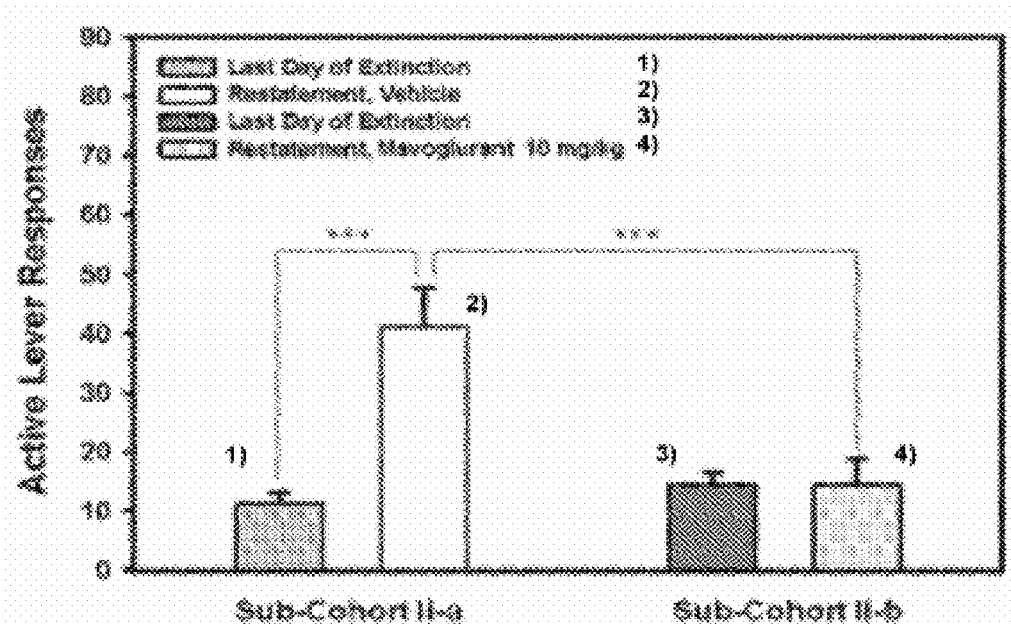
FIG. 4: Effects of mavoglurant (10 mg/kg, PO, 1 hour pre-treatment) on the reinstatement of a cocaine self-administration response in rats. Data are presented as mean+SEM. Asterisks (***: $P<0.001$) indicate a significant difference. N=14-15 per treatment group.

The effects of vehicle and mavoglurant (10 mg/kg, PO, 1 hour prior to test) on cue-induced reinstatement of the self-administration response are illustrated in FIG. 4. Two-way ANOVAs confirmed a significant effect of session (extinction vs. reinstatement, $F[1,54]=12,690$; $P<0.001$), a significant treatment effect (vehicle vs. mavoglurant, $F[1,54]=8.194$; $P<0.01$) and a significant treatment x session interaction ($F[1,54]=12,805$; $P<0.001$). Post hoc analyses indicated that the session effect was solely attributed by vehicle treatment, i.e. while cue induced a significant reinstatement of active lever-pressing ($P<0.001$), cue-induced reinstatement was suppressed in mavoglurant-treated rats.

Conclusions:

The present study investigated the efficacy of mavoglurant in a rat model of cocaine self-administration and a model of relapse for cocaine intake (i.e. cue-induced reinstatement). Mavoglurant (10 mg/kg, PO, 1 hour prior to test) significantly reduced cocaine self-administration in rats.

Moreover, after extinction of the self-administration response, mavoglurant (10 mg/kg, PO, 1 hour prior to test) completely prevented cue-induced reinstatement of the self-administration response.

In conclusion, the present study indicated that mavoglurant is efficacious in a rat model of cocaine self-administration, as well as in a model of relapse.

Example 2

Placebo-Controlled Study in Patients with CUD

| Study objectives and endpoints | |
|---|---|
| Primary objective(s) | Endpoints related to primary objective(s) |
| To evaluate treatment effect of 98-day mavoglurant administration in reducing cocaine use | Proportion of cocaine use days by TLFB cocaine self-report |
| Secondary objective(s) | Endpoints related to secondary objective(s) |
| To assess the effects of 98-day mavoglurant administration versus placebo on:<br>a) other measures of cocaine use<br>b) alcohol use | Urinalysis [cocaine Benzoylecgonine (BE)]<br>b) TLFB alcohol self-report; urinalysis [Ethyl Glucuronide (EtG)] |
| To assess the safety and tolerability of multiple bid oral doses of mavoglurant | Vital signs, ECG parameters, clinical safety laboratory parameters (chemistry/hematology/urinalysis), (serious) adverse events reporting, suicidal ideation [Columbia Suicide Severity Rating Scale (C-SSRS)] |
| To evaluate the pharmacokinetics of mavoglurant | mavoglurant plasma concentrations (pre- and post-dose levels) |
| Exploratory objective(s) | Endpoints related to exploratory objective(s) |
| To assess the frequency of drug and alcohol use before and during 98-day mavoglurant treatment | Hair drug test for cocaine, amphetamine, cannabis, methamphetamine, MDMA, MDEA, MDA, methylphenidate, ketamine and Ethyl glucuronide (EtG) |
| To examine whether individual genetic variation in genes relating to drug metabolism and transporters, CUD and the drug target pathway confer differential response to mavoglurant | genetic markers in pharmacogenetic or biologic candidate genes for CUD, target or drug response |
| To assess the effects of 98-day mavoglurant administration versus placebo on:<br>a) depressive symptoms<br>b) anxiety symptoms<br>c) global functioning | a) Beck's Depression Inventory (BDI)<br>b) State-Trait Anxiety Inventory (STAI)<br>c) Clinical Global Impression Scale - Severity (CGI-S) and Improvement (CGI-I) |

Study Design

Figure 5:
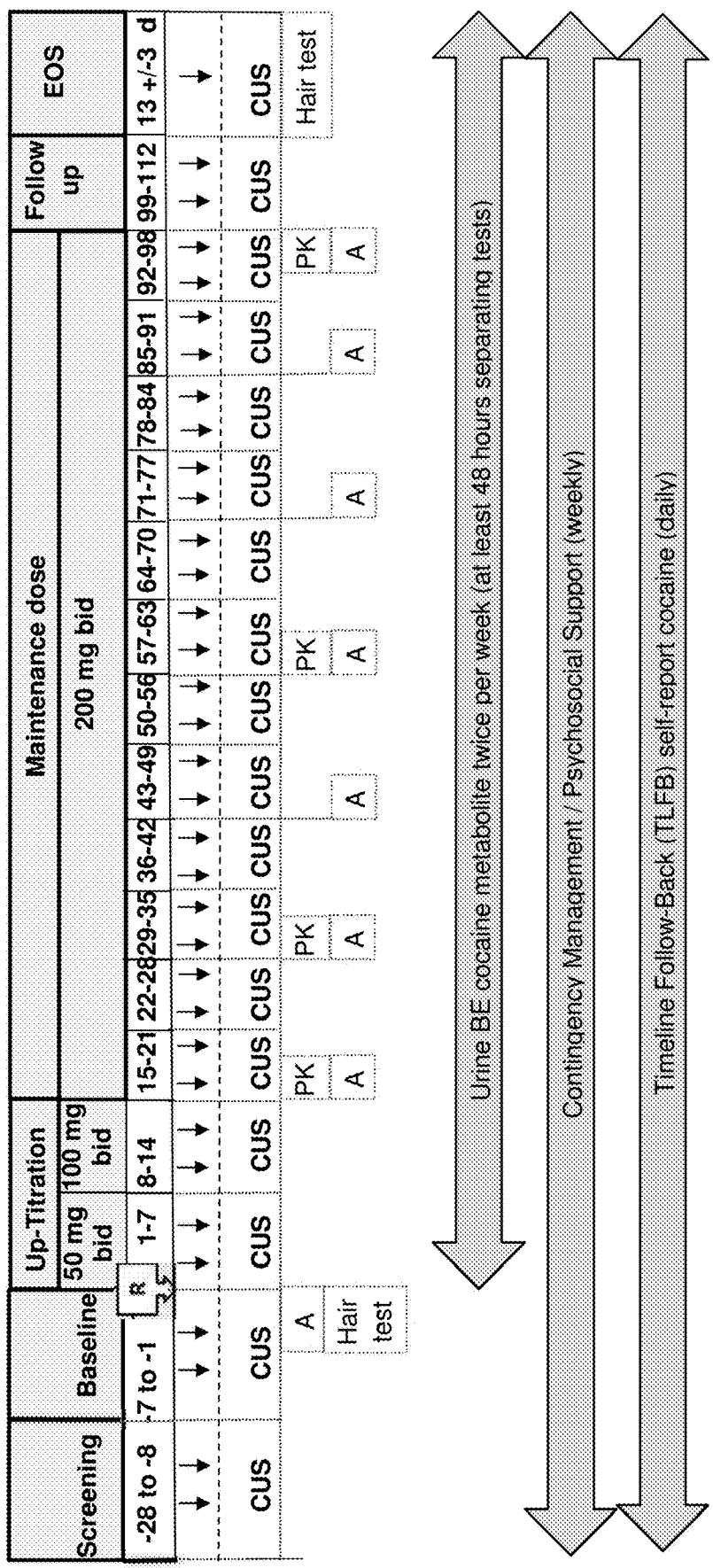
FIG. 5: Shows the design of an approximately 20-weeks study.

This is a randomized, subject and investigator blinded, parallel group, placebo-controlled study in patients with CUD. The study consists of: about 21-day screening period followed by a 7-day baseline; a 98-day out-patient treatment period (14-day up-titration dose regimen followed by 84-day maintenance dose) and finally an end of study visit evaluation approximately 14-days after the last study drug administration. The total duration for each patient in the study is up to approximately 20-weeks. The study design is summarized in FIG. 5.

Study visits: (days 1-112), study visits are performed in an ambulatory setting of frequency twice per week. During these visits the urine samples are collected for drug screen (cocaine BE and others drug metabolites) along with safety/efficacy assessments.

Screening (days −28 to −8): includes safety examinations and other clinical tests, determines patients' initial eligibility. Patients who meet the eligibility criteria at screening are admitted to the baseline evaluation.

Baseline (days −7 to −1): includes, in addition to the safety evaluations, a patient's self-assessment on various scales and questionnaires. During baseline, a history of self-reported cocaine use (TLFB) and two urine samples are collected on two different days with second sample collected 3 days prior randomization to demonstrate the abstinence from cocaine use.

Treatment (days 1-98): following baseline, on Day 1, eligible patients are randomly assigned in a 1:1 ratio to either mavoglurant (free form) or placebo Group A—mavoglurant (free form): up-titration regimen for the first 2 weeks: 50 mg bid from Day 1 to Day 7, 100 mg bid from Day 8 to Day 14, followed by dosing at 200 mg bid for 84-days The dose selected (200 mg b.i.d/modified release formulation) for evaluation in this study has been chosen based on the safety, tolerability and pharmacokinetic data from completed mavoglurant studies.

Group B: matching placebo.

Study drug: taken twice daily (b.i.d.) in the morning and evening (separated by approximately 12 hour intervals) with food. For all ambulatory morning visits that involve any study assessments or PK/urine sample collection, study medication is self-administered by patient at study center and supervised by study personnel. On these days, standard breakfast is served at study center and consumed by the patient during his/her medication intake. During treatment period, patients also undergo assessments with various scales and questionnaires, as well as safety assessments and pharmacokinetic sampling at pre- and 2±1-hour post dose per SoA.

Urine samples (days 1-113): samples are collected at study center twice per week, with at least 48 hours separating tests, e.g. Tuesday and Fridays or Mondays and Thursdays or Tuesday morning and Thursday afternoon. The sample collection is staff-observed and is assayed quantitatively for the presence of cocaine and alcohol metabolites [benzoylecgonine (BE) and Ethyl Glucuronide (EtG)]. Urine samples are collected during study conduct: 28 samples from patients who remain in treatment for the 14 weeks (4 samples in weeks 1-2 of up-titration); 24 samples in weeks 3-14 (maintenance dose); 4 samples in weeks 15-16 (follow up) and finally last 1 sample at end of study visit. If a patient fails to attend the clinic or refuses to provide a sample on a scheduled testing day, samples are considered positive unless an excused absence is granted (e.g. illness, other personal reason). In cases of missed or refused samples, samples are collected on the next day whenever possible.

Clinical Support to Ensure Medication and Protocol's Adherence:

Contingency Management (CM) and psychosocial support: on top of study treatment, all patients receive weekly at site the Contingency Management (CM) therapy with the focus on patients' adherence to the protocol and retention. In addition, they receive also a standardized psychological support at least once a week.

Medication compliance: patients are at the study site at time of study drug administration for the morning dose on PK collection days and on all other days that involves urine sampling assessments. On these days study medication self-administration is supervised by study personnel, compliance is ensured by mouth check after the medication is swallowed. To monitor medication adherence, patients are provided with individual Medication Diary (booklet) to record administration of study medication. Medication compliance is monitored by the investigator and/or study personnel at least on a weekly basis using tablet(s) counts. Dosage adherence is verified by comparing the patient's Medication Diary self-reported data against the total number of tablets in the returned bottle or blister (depends on the packaging form). Adherence is calculated as the total amount of tablets taken divided by the scheduled total amount to be taken during the treatment phase. If the Investigator feels it is appropriate, the patient may also be contacted during the out-patient periods to confirm compliance.

Population

Patients, aged of 18-65 inclusive with a diagnosis of CUD, who use cocaine through snorting (intranasally), are enrolled in the study.

CUD Patients

The investigator ensures that all subjects being considered for the study meet the following eligibility criteria(s). No additional criteria are applied by the investigator. Subject selection is to be established by checking through all eligibility criteria at screening and at baseline. A relevant record (e.g. checklist) of the eligibility criteria is stored with the source documentation at the study site.

Deviation from any entry criterion excludes a subject from enrollment into the study.

Inclusion Criteria

1. Understand the study procedures and provide written informed consent before any assessment is performed.
2. Male and female subjects, 18 to 65 years of age (inclusive) and diagnosed with Cocaine Use Disorder according to DSM 5 (Diagnostic and Statistical Manual of Mental Disorders, 5th Ed.).
3. Must use cocaine through snorting (intranasally).
4. Recent cocaine use confirmed by positive urine screen for 1 or more benzoylecgonine (BE)
5. Must be seeking treatment for cocaine dependence and have a desire to reduce or cease cocaine use as per goals assessed at baseline.
6. Must be abstinent from cocaine use for at least 3 days preceding 1st dosing (Day 1) as assessed by self-report TLFB and two *urinalysis samples at baseline.
   *difference in BE level between two baseline's samples must decrease
7. Must be in good health as determined by medical history, physical examination, at screening.
8. At screening, and baseline, vital signs (systolic and diastolic blood pressure and pulse rate) must be within the acceptable ranges by the investigator considering the cocaine's increasing effect on pulse rate in order for the subject to qualify. Investigator may be guided to use the below ranges:
   systolic blood pressure, 90-150 mmHg
   diastolic blood pressure, 50-90 mmHg
   Three readings are acceptable. At least the one of three reading must be within the acceptable ranges.
9. Patients must be able to:
   communicate well verbally with the Investigator and to understand written instructions
   verbalize a willingness to complete all study procedures
   verbally acknowledge that she/he is able to attend each scheduled visit, and that she/he does not have any already scheduled events or activities that may substantially interfere with study participation Exclusion Criteria
1. History of hypersensitivity to any of the study treatments or excipients or to drugs of similar chemical classes.
2. Has current diagnosis of Substance Use Disorder (according to the DSM 5) on alcohol, *cannabis* or other stimulants, except cocaine.
3. Meets current or lifetime DSM 5 criteria for schizophrenia or any psychotic disorder, or organic mental disorder.
   Notes: Subjects diagnosed with other psychiatric disorders may be included provided that the concurrent treatment for the comorbid psychiatric condition does not interfere with completion of the study or place the patient at heightened risk through participation in the trial.
4. Have current treatment for Substance Use Disorder (e.g.: disulfiram, acamprosate, methyl phenidate, modafinil, topiramate, immediate release dexamfetamine, or baclofen).
5. Requires treatment with any psychoactive medications, including any anti-seizure medications (with an exception of medications used for short-term treatment of insomnia) Note:
   SSRI's are allowed if they have adequate stable dose for at least 1 month prior dosing
6. Use of other investigational drugs at the time of screening, or within 5 half-lives of enrollment, or within 30 days, whichever is longer; or longer if required by local regulations.
7. Pregnant or nursing (lactating) women, where pregnancy is defined as the state of a female after conception and until the termination of gestation, confirmed by a positive hCG laboratory test
8. Women of child-bearing potential, defined as all women physiologically capable of becoming pregnant, unless they are using effective methods* of contraception during dosing and for 30 days after last dosing of study medication.
   *Effective contraception methods include:
   Total abstinence (when this is in line with the preferred and usual lifestyle of the subject). Note: Periodic abstinence (e.g., calendar, ovulation, symptothermal, post-ovulation methods) and withdrawal are not acceptable methods of contraception
   Female sterilization (have had surgical bilateral oophorectomy with or without hysterectomy) or tubal ligation at least six weeks before taking study treatment. Note: In case of oophorectomy alone, only when the reproductive status of the woman has been confirmed by follow up hormone level assessment
   Male sterilization (at least 6 months prior to screening). For female subjects on the study, the vasectomized male partner must be the sole partner for that subject
   Barrier methods of contraception: Condom or Occlusive cap (diaphragm orcervical/vault caps) with spermicidal foam/gel/film/cream/vaginal suppository;
   Placement of an intrauterine device (IUD) or intrauterine system (IUS)
   Hormonal contraceptives that are injected or implanted or administered orally or transdermally cannot be considered as effective methods of contraception if taken with study medication.
   Women are considered post-menopausal and not of child bearing potential if they have had 12 months of natural (spontaneous) amenorrhea with an appropriate clinical profile (e.g. age appropriate, history of vasomotor symptoms)
9. History of *Porphyria*.
10. History or presence of malignancy of any organ system, (other than localized basal cell carcinoma of the skin or in-situ cervical cancer), treated or untreated, within the past 5 years, regardless of whether there is evidence of local recurrence or metastases
11. Have a history of any illness, condition, and use of medications that in the opinion of the investigator or designee might confound the results of the study or pose additional risk in administering the investigational agents to the subject or preclude successful completion of the study
12. Any surgical or medical condition which might significantly alter the absorption, distribution, metabolism, or excretion of drugs, or which may jeopardize the subject in case of participation in the study. The Investigator makes this determination in consideration of the subject's medical history and/or clinical or laboratory evidence of the following, at screening:
    Clinical laboratory values (including AST, ALT, total bilirubin or creatinine) considered as not clinically acceptable for CUD population, in the opinion of the Investigator, at screening:
      ALT, serum bilirubin must not exceed 2×ULN
      GGT, AST and alkaline phosphatase must not exceed 5×ULN.
    In the case where a safety laboratory assessment at screening is outside of the range specified above, the assessment may be repeated once prior to randomization. If the repeat value remains outside of the specified ranges, the subject is excluded from the study.
13. Current or/and previous treatment with concomitant medications that are strong or moderate inducers/inhibitors of CYP3A4 (e.g., Clarithromycin, ketoconazole, ritonavir, etc.)
14. Concomitant use of agents known to prolong the QT interval unless these can be permanently discontinued for the duration of study.
15. History or current diagnosis of ECG abnormalities, at screening or baseline, indicating significant risk of safety for subjects participating in the study such as:
    Concomitant clinically significant cardiac arrhythmias, e.g. sustained ventricular tachycardia, and clinically significant second or third degree AV block without a pacemaker
    History of familial long QT syndrome or known family history of Torsades de Pointes
    QTcF>450 msec (males); QTcF>460 msec (females)
    Note: sinus tachycardia, left axis deviation, and non-specific ST or T wave changes are not exclusionary
16. Known history or presence of cardiovascular or cerebrovascular disease such as: angina pectoris, myocardial infarction, stroke, transient ischemic attack, peripheral vascular disease.
17. History of immunodeficiency diseases, including a positive HIV (ELISA and Western blot) test result.
18. Chronic infection with Hepatitis B (HBV) or Hepatitis C (HCV).
19. Score "yes" on item 4 or item 5 of the Suicidal Ideation section of the C-SSRS, if this ideation occurred in the past 6 months, or "yes" on any item of the Suicidal Behavior section, except for the "Non-Suicidal Self-Injurious Behavior" (item also included in the Suicidal Behavior section), if this behavior occurred in the past 2 years.
20. Patient cannot:
anticipate any significant problems with transportation arrangements or available time to travel to the study site and have any plans to move within the next months to a location which would make continued participation in the study impractical
be involved in any unresolved legal problems that could jeopardize continuation or completion of the study Statistical Model and Method of Analysis The primary variable: is the proportion of cocaine use days during the treatment period (days 1-98).

For each patient, the proportion of cocaine use days is calculated by dividing the number of days of cocaine use during the treatment period, i.e. 98 days for completers and number of days between Day 1 and day of last dose in case of premature discontinuation of study treatment. It is considered as a continuous variable. The cocaine consumption is recorded daily (Yes/No) using the TLFB during the entire study.

A Bayesian analysis is conducted on the proportion of cocaine use days. It is assumed to be a continuous outcome with normally distributed errors. A linear model with treatment factor and past consumption of cocaine as covariate is fitted. Non informative priors are used for all parameters. The past consumption of cocaine is the proportion of cocaine use days over the 3 months preceding the screening visit, which is assessed using the TLFB. The model evaluates the posterior probability that the difference in the proportions of cocaine use days between mavoglurant and placebo is <0 and that it's <−10%. The difference of 10% of days is deemed the minimal clinically relevant effect and a difference of 20% is a very promising effect, based on the literature in this indication. The study shows a positive signal of efficacy if the 2 following criteria are met:
1. there is at least 90% probability that the difference in the proportions of cocaine use days between mavoglurant and placebo is <0
2. there is at least 50% probability that the difference in the proportions of cocaine use days between mavoglurant and placebo is <−10%

Sensitivity analyses are performed using other models, like negative binomial regression if the distribution of the data is not normal. Additionally, the profiles of consumption over time are compared between treatment groups through analyses of longitudinal data (weekly use) using mixed models for repeated measures.

The secondary variables: include the proportion of negative UDS over the treatment period and will be analyzed in the same way as the primary variable. Safety and PK are secondary endpoints for this study.

The invention claimed is:

1. A method for the reduction of cocaine use by a cocaine use disorder patient, in need thereof, comprising administering to said cocaine use disorder patient an effective amount of mavoglurant, or a pharmaceutically acceptable salt thereof, wherein the amount and/or frequency of cocaine use by the cocaine use disorder patient is reduced, and
wherein mavoglurant, or a pharmaceutically acceptable salt thereof, is administered in an amount of 200 mg/b.i.d.

2. A method according to claim 1, wherein cocaine use disorder comprises cocaine inhalation (i.e. smoking), intravenous cocaine, cocaine nasal insufflation (i.e. snorting) or oral formulations of cocaine.

3. A method according to claim 1, wherein cocaine use disorder is comorbid with a psychiatric disorder.

4. A method according to claim 1, wherein administration of mavoglurant, or a pharmaceutically acceptable salt thereof, is combined with standardized psychological treatment.

5. A method according to claim 1, wherein administration of mavoglurant, or a pharmaceutically acceptable salt thereof, is combined with psychosocial or behavioral therapy or combination thereof.

6. A method according to claim 5, wherein the psychosocial or the behavioral therapy is computer-assisted.

7. A method according to claim 1, wherein administration of mavoglurant, or a pharmaceutically acceptable salt thereof, is concomitant with methadone or buprenorphine treatment.

8. A method according to claim 1, wherein mavoglurant, or a pharmaceutically acceptable salt thereof, is administered in combination with a further active agent.

9. A method according to claim 1, wherein the patient has a genetic variation associated with a substance use disorder.

10. A method according to claim 1, wherein mavoglurant, or a pharmaceutically acceptable salt thereof, is administered in an immediate-release form or a modified-release form.

11. A method according to claim 3, wherein the psychiatric disorder is chosen from antisocial personality disorder, borderline personality disorder, depression, anxiety, schizophrenia, attention deficit hyperactivity disorder, bipolar disorder, obsessive compulsive disorder, and binge eating disorder.

12. A method according to claim 1, wherein administration of mavoglurant, or a pharmaceutically acceptable salt thereof, is combined with contingency management based therapy.

13. A method according to claim 1, wherein the patient has a genetic variation associated with cocaine use disorder.

* * * * *